(12) United States Patent
Longinotti-Buitoni

(10) Patent No.: US 10,154,791 B2
(45) Date of Patent: Dec. 18, 2018

(54) BIOMETRIC IDENTIFICATION BY GARMENTS HAVING A PLURALITY OF SENSORS

(71) Applicant: Gianluigi Longinotti-Buitoni, Haute-Nendaz (CH)

(72) Inventor: Gianluigi Longinotti-Buitoni, Haute-Nendaz (CH)

(73) Assignee: L.I.F.E. Corporation S.A., Luxembourg (LU)

( * ) Notice: Subject to any disclaimer, the term of this patent is extended or adjusted under 35 U.S.C. 154(b) by 0 days.

(21) Appl. No.: 15/640,963

(22) Filed: Jul. 3, 2017

(65) Prior Publication Data

US 2018/0000367 A1 Jan. 4, 2018

Related U.S. Application Data

(60) Provisional application No. 62/357,665, filed on Jul. 1, 2016.

(51) Int. Cl.
*A61B 5/04* (2006.01)
*A61B 5/117* (2016.01)
(Continued)

(52) U.S. Cl.
CPC ............ *A61B 5/04* (2013.01); *A41D 13/1281* (2013.01); *A61B 5/0428* (2013.01); *A61B 5/053* (2013.01); *A61B 5/117* (2013.01); *A61B 5/6804* (2013.01); *A61B 5/6805* (2013.01); *G06F 21/32* (2013.01); *G06K 9/00892* (2013.01); *G06K 9/00906* (2013.01); *G06K 9/4609* (2013.01); *A61B 5/0024* (2013.01); *A61B 5/0205* (2013.01); *A61B 5/0404* (2013.01); *A61B 5/0488* (2013.01); *A61B 5/0816* (2013.01);
(Continued)

(58) Field of Classification Search
CPC ......... A61B 5/04; A61B 5/053; A61B 5/0428; A61B 5/6804; A61B 5/0024; A61B 5/0205; A61B 5/0404; A61B 5/11; A61B 5/6805; G06K 9/4609; G06K 9/00906; A41D 13/1281; G06F 21/32
USPC ...................................................... 340/5.82
See application file for complete search history.

(56) References Cited

U.S. PATENT DOCUMENTS

| 3,591,526 A | 7/1971 | Kawashima |
| 3,793,716 A | 2/1974 | Smith |

(Continued)

FOREIGN PATENT DOCUMENTS

| EP | 1057923 A1 | 12/2000 |
| EP | 1335831 A1 | 8/2003 |

(Continued)

OTHER PUBLICATIONS

Longinotti-Buitoni et al.; U.S. Appl. No. 15/554,784 entitled "Laundry system for smart garments," filed Aug. 31, 2017.

(Continued)

*Primary Examiner* — Ali Neyzari
(74) *Attorney, Agent, or Firm* — Shay Glenn LLP

(57) ABSTRACT

Biometric identification methods and apparatuses (including devices and systems) for uniquely identifying one an individual based on wearable garments including a plurality of sensors, including but not limited to sensors having multiple sensing modalities (e.g., movement, respiratory movements, heart rate, ECG, EEG, etc.).

21 Claims, 13 Drawing Sheets

(51) Int. Cl.
*G06F 21/32* (2013.01)
*G06K 9/00* (2006.01)
*A41D 13/12* (2006.01)
*A61B 5/0428* (2006.01)
*A61B 5/053* (2006.01)
*G06K 9/46* (2006.01)
*A61B 5/00* (2006.01)
*A61B 5/0205* (2006.01)
*A61B 5/0404* (2006.01)
*A61B 5/0488* (2006.01)
*A61B 5/08* (2006.01)
*A61B 5/11* (2006.01)

(52) U.S. Cl.
CPC ......... *A61B 5/11* (2013.01); *A61B 2562/0219* (2013.01); *G06K 2009/00939* (2013.01)

(56) References Cited

U.S. PATENT DOCUMENTS

| | | |
|---|---|---|
| 4,624,817 A | 11/1986 | Gusack et al. |
| 4,710,981 A | 12/1987 | Sanchez |
| 4,823,240 A | 4/1989 | Shenker |
| 4,867,166 A | 9/1989 | Axelgaard et al. |
| 5,036,865 A | 8/1991 | Keaton |
| 5,111,818 A | 5/1992 | Suzuki et al. |
| 5,148,002 A | 9/1992 | Kuo et al. |
| 5,163,006 A | 11/1992 | Deziel |
| 5,241,300 A | 8/1993 | Buschmann |
| 5,280,265 A | 1/1994 | Kramer et al. |
| 5,352,315 A | 10/1994 | Carrier et al. |
| 5,379,461 A | 1/1995 | Wilmers |
| 5,395,508 A | 3/1995 | Jolly et al. |
| 5,557,263 A | 9/1996 | Fisher et al. |
| 5,581,492 A | 12/1996 | Janik |
| 5,635,909 A | 6/1997 | Cole |
| 5,678,448 A | 10/1997 | Fullen et al. |
| 5,694,645 A | 12/1997 | Triplette |
| 5,749,365 A | 5/1998 | Magill |
| 5,802,607 A | 9/1998 | Triplette |
| 5,824,996 A | 10/1998 | Kochman et al. |
| 5,845,644 A | 12/1998 | Hughes et al. |
| 5,853,005 A | 12/1998 | Scanlon |
| 5,865,740 A | 2/1999 | Kelly et al. |
| 5,903,222 A | 5/1999 | Kawarizadeh et al. |
| 5,906,004 A | 5/1999 | Lebby et al. |
| 5,912,653 A | 6/1999 | Fitch |
| 5,921,674 A | 7/1999 | Koczi |
| 6,016,476 A | 1/2000 | Maes et al. |
| 6,019,877 A | 2/2000 | Dupelle et al. |
| 6,024,575 A | 2/2000 | Ulrich |
| 6,047,203 A | 4/2000 | Sackner et al. |
| 6,080,690 A | 6/2000 | Lebby et al. |
| 6,097,297 A | 8/2000 | Fard |
| 6,136,127 A | 10/2000 | De Bastiani |
| 6,144,120 A | 11/2000 | Doi et al. |
| 6,210,771 B1 | 4/2001 | Post et al. |
| 6,232,879 B1 | 5/2001 | Tyren |
| 6,259,399 B1 | 7/2001 | Krasner |
| 6,319,015 B1 | 11/2001 | Faunce |
| 6,325,066 B1 | 12/2001 | Hughes et al. |
| 6,341,504 B1 | 1/2002 | Istook |
| 6,349,201 B1 | 2/2002 | Ford |
| 6,415,176 B1 | 7/2002 | Scheirer et al. |
| 6,436,064 B1 | 8/2002 | Kloecker |
| 6,490,534 B1 | 12/2002 | Pfister |
| 6,561,814 B2 | 5/2003 | Tilbury et al. |
| 6,563,424 B1 | 5/2003 | Kaario |
| 6,642,467 B2 | 11/2003 | Farringdon |
| 6,668,380 B2 | 12/2003 | Marmaropolous et al. |
| 6,713,733 B2 | 3/2004 | Kochman et al. |
| 6,729,025 B2 | 5/2004 | Farrell et al. |
| 6,792,124 B2 | 9/2004 | Tilbury et al. |
| 6,801,140 B2 | 10/2004 | Mantyjarvi et al. |
| 6,830,344 B2 | 12/2004 | Reho et al. |
| 6,895,261 B1 | 5/2005 | Palamides |
| 6,930,608 B2 | 8/2005 | Grajales et al. |
| 6,968,075 B1 | 11/2005 | Chang |
| 6,970,731 B1 | 11/2005 | Jayaraman et al. |
| 6,982,115 B2 | 1/2006 | Poulos et al. |
| 7,020,508 B2 | 3/2006 | Stivoric et al. |
| 7,034,685 B2 | 4/2006 | Fabre et al. |
| 7,161,084 B2 | 1/2007 | Sandbach |
| 7,173,437 B2 | 2/2007 | Hervieux et al. |
| 7,191,803 B2 | 3/2007 | Orr et al. |
| 7,210,939 B2 | 5/2007 | Marmaropolous et al. |
| 7,211,053 B2 | 5/2007 | Marmaropolous et al. |
| 7,230,610 B2 | 6/2007 | Jung et al. |
| 7,248,756 B2 | 7/2007 | Ebbesen et al. |
| 7,250,547 B1 | 7/2007 | Hofmeister et al. |
| 7,299,034 B2 | 11/2007 | Kates |
| 7,299,964 B2 | 11/2007 | Jayaraman et al. |
| 7,319,895 B2 | 1/2008 | Klefstad-Sillonville et al. |
| 7,320,947 B2 | 1/2008 | Child et al. |
| 7,321,785 B2 | 1/2008 | Harris |
| 7,324,841 B2 | 1/2008 | Reho et al. |
| 7,344,379 B2 | 3/2008 | Marmaropolous et al. |
| 7,348,645 B2 | 3/2008 | Xu |
| 7,365,031 B2 | 4/2008 | Swallow et al. |
| 7,377,133 B2 | 5/2008 | Sandbach et al. |
| 7,388,166 B2 | 6/2008 | Marmaropolous et al. |
| 7,429,959 B2 | 9/2008 | Gerder et al. |
| 7,448,874 B2 | 11/2008 | Willis |
| 7,476,104 B2 | 1/2009 | Marmaropolous et al. |
| 7,559,768 B2 | 7/2009 | Marmaropolous et al. |
| 7,578,195 B2 | 8/2009 | DeAngelis et al. |
| 7,616,112 B2 | 11/2009 | Miller, III |
| 7,645,220 B2 | 1/2010 | Hoffman et al. |
| 7,665,288 B2 | 2/2010 | Karayianni et al. |
| 7,683,643 B2 | 3/2010 | Qi et al. |
| 7,712,373 B2 | 5/2010 | Nagle et al. |
| 7,715,873 B1 | 5/2010 | Biere et al. |
| 7,719,007 B2 | 5/2010 | Thompkins et al. |
| 7,732,002 B2 | 6/2010 | Kodas et al. |
| 7,753,685 B2 | 7/2010 | Lee et al. |
| 7,753,845 B2 | 7/2010 | Gopinathan et al. |
| 7,760,082 B2 | 7/2010 | Wong et al. |
| 7,769,412 B1 | 8/2010 | Gailloux |
| 7,770,473 B2 | 8/2010 | Von Lilienfeld-Toal et al. |
| 7,779,656 B2 | 8/2010 | Dias et al. |
| 7,783,334 B2 | 8/2010 | Nam et al. |
| 7,787,726 B2 | 8/2010 | Ten Eyck et al. |
| 7,849,888 B2 | 12/2010 | Karayianni et al. |
| 7,862,624 B2 | 1/2011 | Tran |
| 7,870,761 B2 | 1/2011 | Valentine et al. |
| 7,872,557 B2 | 1/2011 | Seibert |
| 7,878,030 B2 | 2/2011 | Burr |
| 7,880,607 B2 | 2/2011 | Olson et al. |
| 7,891,020 B2 | 2/2011 | Von Bluecher |
| 7,914,108 B2 | 3/2011 | Konno et al. |
| 7,933,554 B2 | 4/2011 | Hoyt et al. |
| 7,955,696 B2 | 6/2011 | Baikerikar et al. |
| 7,976,480 B2 | 7/2011 | Grajales et al. |
| 7,982,613 B2 | 7/2011 | Zheng |
| 7,983,876 B2 | 7/2011 | Vock et al. |
| 8,008,606 B2 | 8/2011 | Kaiserman et al. |
| 8,024,023 B2 | 9/2011 | Tolvanen |
| 8,032,199 B2 | 10/2011 | Linti et al. |
| 8,063,307 B2 | 11/2011 | Bukshpun et al. |
| 8,099,258 B2 | 1/2012 | Alten et al. |
| 8,140,143 B2 | 3/2012 | Picard et al. |
| 8,146,171 B2 | 4/2012 | Chung et al. |
| 8,162,857 B2 | 4/2012 | Lanfermann et al. |
| 8,186,231 B2 | 5/2012 | Graumann et al. |
| 8,214,008 B2 | 7/2012 | Hassonjee et al. |
| 8,228,202 B2 | 7/2012 | Buchner et al. |
| 8,253,586 B1 | 8/2012 | Matak |
| 8,262,217 B2 | 9/2012 | Furukawa |
| 8,263,215 B2 | 9/2012 | Burr et al. |
| 8,267,862 B2 | 9/2012 | Jeong et al. |
| 8,308,489 B2 | 11/2012 | Lee et al. |
| 8,331,097 B2 | 12/2012 | Yang et al. |
| 8,340,740 B2 | 12/2012 | Holzer et al. |

(56) References Cited

U.S. PATENT DOCUMENTS

| | | |
|---|---|---|
| 8,348,841 B2 | 1/2013 | Varadan |
| 8,348,865 B2 | 1/2013 | Jeong et al. |
| 8,362,882 B2 | 1/2013 | Heubel et al. |
| 8,373,079 B2 | 2/2013 | Walkington |
| 8,398,546 B2 | 3/2013 | Pacione et al. |
| 8,403,845 B2 | 3/2013 | Stivoric et al. |
| 8,416,579 B2 | 4/2013 | Biesheuvel et al. |
| 8,475,371 B2 | 7/2013 | Derchak et al. |
| 8,739,397 B2 | 6/2014 | Nagata et al. |
| 8,862,431 B2 | 10/2014 | Hodge |
| 8,926,393 B2 | 1/2015 | Cannard et al. |
| 8,945,328 B2 | 2/2015 | Longinotti-Buitoni et al. |
| 8,948,839 B1 | 2/2015 | Longinotti-Buitoni et al. |
| 8,954,129 B1 | 2/2015 | Schlegel et al. |
| 9,282,893 B2 | 3/2016 | Longinotti-Buitoni et al. |
| 9,566,032 B2 | 2/2017 | Babaeizadeh et al. |
| 9,979,547 B2 * | 5/2018 | Starner ................ H04L 9/3231 |
| 2002/0093515 A1 | 7/2002 | Fay et al. |
| 2003/0139692 A1 | 7/2003 | Barrey et al. |
| 2004/0115430 A1 | 6/2004 | Leonard |
| 2004/0249242 A1 | 12/2004 | Lau et al. |
| 2005/0029680 A1 | 2/2005 | Jung et al. |
| 2005/0058744 A1 | 3/2005 | Steinberg et al. |
| 2005/0067816 A1 | 3/2005 | Buckman |
| 2005/0107722 A1 | 5/2005 | Ozaki et al. |
| 2005/0228234 A1 | 10/2005 | Yang |
| 2006/0007059 A1 | 1/2006 | Bell |
| 2006/0062993 A1 | 3/2006 | Ogata et al. |
| 2006/0080182 A1 | 4/2006 | Thompson et al. |
| 2006/0124470 A1 | 6/2006 | Zama et al. |
| 2006/0139165 A1 | 6/2006 | Bader |
| 2006/0155182 A1 | 7/2006 | Mazzarolo |
| 2007/0000912 A1 | 1/2007 | Aisenbrey |
| 2007/0046720 A1 | 3/2007 | Konno et al. |
| 2007/0049842 A1 | 3/2007 | Hill et al. |
| 2007/0151312 A1 | 7/2007 | Bruce et al. |
| 2007/0153363 A1 | 7/2007 | Gruner |
| 2007/0177770 A1 | 8/2007 | Derchak et al. |
| 2007/0178716 A1 | 8/2007 | Glaser et al. |
| 2007/0202765 A1 | 8/2007 | Krans et al. |
| 2007/0293781 A1 | 12/2007 | Sims et al. |
| 2008/0045815 A1 | 2/2008 | Derchak et al. |
| 2008/0058744 A1 | 3/2008 | Tippey et al. |
| 2008/0064964 A1 | 3/2008 | Nagata et al. |
| 2008/0083720 A1 | 4/2008 | Gentile et al. |
| 2008/0083721 A1 | 4/2008 | Kaiserman et al. |
| 2008/0083740 A1 | 4/2008 | Kaiserman et al. |
| 2008/0171914 A1 | 7/2008 | Ouwerkerk et al. |
| 2008/0177168 A1 | 7/2008 | Callahan et al. |
| 2008/0234561 A1 | 9/2008 | Roesicke et al. |
| 2008/0241391 A1 | 10/2008 | Kim et al. |
| 2008/0246629 A1 | 10/2008 | Tsui et al. |
| 2008/0255794 A1 | 10/2008 | Levine |
| 2008/0258921 A1 | 10/2008 | Woo et al. |
| 2008/0269629 A1 | 10/2008 | Reiner |
| 2008/0269652 A1 | 10/2008 | Reiner |
| 2008/0287769 A1 | 11/2008 | Kurzweil et al. |
| 2008/0287770 A1 | 11/2008 | Kurzweil et al. |
| 2008/0294019 A1 | 11/2008 | Tran |
| 2009/0012408 A1 | 1/2009 | Nagata et al. |
| 2009/0018410 A1 | 1/2009 | Coene et al. |
| 2009/0105795 A1 | 4/2009 | Minogue et al. |
| 2009/0112078 A1 | 4/2009 | Tabe |
| 2009/0157327 A1 | 6/2009 | Nissila |
| 2009/0227856 A1 | 9/2009 | Russell et al. |
| 2009/0281394 A1 | 11/2009 | Russell et al. |
| 2009/0286055 A1 | 11/2009 | Pourdeyhimi et al. |
| 2010/0004720 A1 | 1/2010 | Li et al. |
| 2010/0029598 A1 | 2/2010 | Kopitz et al. |
| 2010/0041974 A1 | 2/2010 | Ting et al. |
| 2010/0059274 A1 | 3/2010 | Ives et al. |
| 2010/0071205 A1 | 3/2010 | Graumann et al. |
| 2010/0077528 A1 | 4/2010 | Lind et al. |
| 2010/0112195 A1 | 5/2010 | Kodas et al. |
| 2010/0113910 A1 | 5/2010 | Brauers et al. |
| 2010/0149567 A1 | 6/2010 | Kanazawa et al. |
| 2010/0185062 A1 | 7/2010 | Salazar et al. |
| 2010/0185398 A1 | 7/2010 | Berns et al. |
| 2010/0194815 A1 | 8/2010 | Furukawa |
| 2010/0198038 A1 | 8/2010 | Nagata et al. |
| 2010/0234715 A1 | 9/2010 | Shin et al. |
| 2010/0274100 A1 | 10/2010 | Behar et al. |
| 2010/0292598 A1 | 11/2010 | Roschk et al. |
| 2010/0309209 A1 | 12/2010 | Hodgins et al. |
| 2010/0312071 A1 | 12/2010 | Schenk |
| 2010/0324405 A1 | 12/2010 | Niemi et al. |
| 2011/0000412 A1 | 1/2011 | Chung et al. |
| 2011/0015498 A1 | 1/2011 | Mestrovic et al. |
| 2011/0032103 A1 | 2/2011 | Bhat et al. |
| 2011/0042125 A1 | 2/2011 | Lee et al. |
| 2011/0087115 A1 | 4/2011 | Sackner et al. |
| 2011/0092795 A1 | 4/2011 | Derchak |
| 2011/0100683 A1 | 5/2011 | Bhattacharya et al. |
| 2011/0102304 A1 | 5/2011 | Nelson |
| 2011/0115624 A1 | 5/2011 | Tran |
| 2011/0125064 A1 | 5/2011 | Shyr |
| 2011/0130643 A1 | 6/2011 | Derchak et al. |
| 2011/0144457 A1 | 6/2011 | Coulon |
| 2011/0183068 A1 | 7/2011 | Yamakawa et al. |
| 2011/0184270 A1 | 7/2011 | Russell et al. |
| 2011/0259638 A1 | 10/2011 | Sherrill et al. |
| 2011/0267578 A1 | 11/2011 | Wilson |
| 2011/0277206 A1 | 11/2011 | Sokolowski |
| 2011/0288605 A1 | 11/2011 | Kaib et al. |
| 2012/0024833 A1 | 2/2012 | Klewer et al. |
| 2012/0029299 A1 | 2/2012 | Deremer et al. |
| 2012/0030935 A1 | 2/2012 | Slade et al. |
| 2012/0031431 A1 | 2/2012 | Carlson et al. |
| 2012/0035426 A1 | 2/2012 | Mielcarz et al. |
| 2012/0071039 A1 | 3/2012 | Debock et al. |
| 2012/0071793 A1 | 3/2012 | Gal |
| 2012/0078127 A1 | 3/2012 | McDonald et al. |
| 2012/0088986 A1 | 4/2012 | David et al. |
| 2012/0118427 A1 | 5/2012 | Brookstein et al. |
| 2012/0127687 A1 | 5/2012 | Allee et al. |
| 2012/0136231 A1 | 5/2012 | Markel |
| 2012/0143093 A1 | 6/2012 | Stirling et al. |
| 2012/0144551 A1 | 6/2012 | Guldalian |
| 2012/0144561 A1 | 6/2012 | Begriche et al. |
| 2012/0144934 A1 | 6/2012 | Russell et al. |
| 2012/0146797 A1 | 6/2012 | Oskin et al. |
| 2012/0158074 A1 | 6/2012 | Hall |
| 2012/0165645 A1 | 6/2012 | Russell et al. |
| 2012/0165717 A1 | 6/2012 | Al Khaburi |
| 2012/0184826 A1 | 7/2012 | Keenan et al. |
| 2012/0188158 A1 | 7/2012 | Tan et al. |
| 2012/0197224 A1 | 8/2012 | Chagger |
| 2012/0215076 A1 | 8/2012 | Yang et al. |
| 2012/0223833 A1 | 9/2012 | Thomas et al. |
| 2012/0233751 A1 | 9/2012 | Hexels |
| 2012/0238845 A1 | 9/2012 | Yang |
| 2012/0246795 A1 | 10/2012 | Scheffler et al. |
| 2012/0255166 A1 | 10/2012 | Kim et al. |
| 2012/0324616 A1 | 12/2012 | Hyde et al. |
| 2012/0330109 A1 | 12/2012 | Tran |
| 2013/0013331 A1 | 1/2013 | Horseman |
| 2013/0019372 A1 | 1/2013 | Esses |
| 2013/0019383 A1 | 1/2013 | Korkala et al. |
| 2013/0041272 A1 | 2/2013 | Guillen et al. |
| 2013/0053674 A1 | 2/2013 | Volker |
| 2013/0066168 A1 | 3/2013 | Yang et al. |
| 2013/0072777 A1 | 3/2013 | Tremblay |
| 2013/0077263 A1 | 3/2013 | Oleson et al. |
| 2013/0079860 A1 | 3/2013 | Besio |
| 2013/0144111 A1 | 6/2013 | Wang et al. |
| 2013/0179288 A1 | 7/2013 | Moses et al. |
| 2013/0211208 A1 | 8/2013 | Varadan |
| 2013/0212900 A1 | 8/2013 | Stewart |
| 2013/0231711 A1 * | 9/2013 | Kaib ................... G06F 19/3418 607/5 |
| 2013/0244121 A1 | 9/2013 | Gogotsi et al. |
| 2013/0245423 A1 | 9/2013 | Derchak et al. |
| 2013/0281795 A1 | 10/2013 | Varadan |
| 2013/0314668 A1 | 11/2013 | Haddadi et al. |

(56) References Cited

U.S. PATENT DOCUMENTS

| | | |
|---|---|---|
| 2014/0061273 A1 | 3/2014 | Bullivant et al. |
| 2014/0100436 A1 | 4/2014 | Brunner et al. |
| 2014/0135593 A1 | 5/2014 | Jayalth et al. |
| 2014/0182880 A1 | 7/2014 | Simenhaus et al. |
| 2014/0206948 A1 | 7/2014 | Romem |
| 2014/0303470 A1 | 10/2014 | Tsukada et al. |
| 2014/0312027 A1 | 10/2014 | Augustine et al. |
| 2015/0143601 A1 | 5/2015 | Longinotti-Buitoni et al. |
| 2015/0250420 A1 | 9/2015 | Longinotti-Buitoni et al. |
| 2015/0289820 A1 | 10/2015 | Miller et al. |
| 2016/0262462 A1* | 9/2016 | Kawamura .......... A01K 13/006 |
| 2016/0314576 A1 | 10/2016 | Aliverti et al. |
| 2017/0112440 A1 | 4/2017 | Mauri et al. |
| 2017/0196513 A1 | 7/2017 | Longinotti-Buitoni et al. |

FOREIGN PATENT DOCUMENTS

| | | |
|---|---|---|
| EP | 1478249 A1 | 11/2004 |
| EP | 1509128 A1 | 3/2005 |
| EP | 1622512 A2 | 2/2006 |
| EP | 1709903 A1 | 10/2006 |
| EP | 1905112 A2 | 4/2008 |
| EP | 1907075 A2 | 4/2008 |
| EP | 1925718 A2 | 5/2008 |
| EP | 2025369 A2 | 2/2009 |
| EP | 2191737 A1 | 6/2010 |
| EP | 2196142 A1 | 6/2010 |
| EP | 2217145 A1 | 8/2010 |
| EP | 2314744 A2 | 4/2011 |
| EP | 3037036 A1 | 6/2016 |
| WO | WO90/06189 A1 | 6/1990 |
| WO | WO00/16493 A1 | 3/2000 |
| WO | WO01/01855 A1 | 1/2001 |
| WO | WO03/000015 A2 | 1/2003 |
| WO | WO03/060449 A1 | 7/2003 |
| WO | WO2004/076731 A1 | 9/2004 |
| WO | WO2004/107831 A2 | 12/2004 |
| WO | WO2005/032447 A2 | 4/2005 |
| WO | WO2005/067796 A1 | 7/2005 |
| WO | WO2005/096133 A1 | 10/2005 |
| WO | WO2006/064447 A2 | 6/2006 |
| WO | WO2006/102538 A2 | 9/2006 |
| WO | WO2007/056557 A1 | 5/2007 |
| WO | WO2008/137046 A1 | 11/2008 |
| WO | WO2008/153786 A1 | 12/2008 |
| WO | WO2009/040696 A1 | 4/2009 |
| WO | WO2009/112281 A1 | 9/2009 |
| WO | WO2010/038176 A1 | 4/2010 |
| WO | WO2010/044018 A1 | 4/2010 |
| WO | WO2010/058346 A2 | 5/2010 |
| WO | WO20 0/085671 A1 | 7/2010 |
| WO | WO2010/085688 A1 | 7/2010 |
| WO | WO2010/096907 A1 | 9/2010 |
| WO | WO2010/120945 A1 | 10/2010 |
| WO | WO2011/092620 A1 | 8/2011 |
| WO | WO2011/156095 A2 | 12/2011 |
| WO | WO2012/011068 A1 | 1/2012 |
| WO | WO2012/060524 A1 | 5/2012 |
| WO | WO2012/066056 A1 | 5/2012 |
| WO | WO2012/073076 A1 | 6/2012 |
| WO | WO2012/073230 A1 | 6/2012 |
| WO | WO2012/083066 A2 | 6/2012 |
| WO | WO2012/104484 A1 | 8/2012 |
| WO | WO2012/110954 A1 | 8/2012 |
| WO | WO2012/112186 A1 | 8/2012 |
| WO | WO2012/113014 A1 | 8/2012 |
| WO | WO2012/140079 A1 | 10/2012 |
| WO | WO2012/140522 A2 | 10/2012 |
| WO | WO2012/168836 A2 | 12/2012 |
| WO | WO2012/176193 A1 | 12/2012 |
| WO | WO2014/025430 A2 | 2/2014 |
| WO | WO2014/075682 A1 | 5/2014 |
| WO | WO2014/204323 A1 | 12/2014 |
| WO | WO2015/103620 A1 | 7/2015 |
| WO | WO2015/138515 A1 | 9/2015 |
| WO | WO2016/035350 A1 | 3/2016 |

OTHER PUBLICATIONS

Longinotti-Buitoni et al.; U.S. Appl. No. 15/813,073 entitled "Garments having stretchable and conductive ink," filed Nov. 14, 2017.

Aliverti et al.; Compartmental analysis of breathing in the supine and prone positions by optoelectronic plethysmography; Ann Biomed Eng; 29(1):60-70; Jan. 2001.

Babchenko et al.; Fiber optic sensor for the measurement of respiratory chest circumference changes; J Biomed Opt; 4(2):224-229; Apr. 1999.

Cala et al.; Chest wall and lung volume estimation by optical reflectance motion analysis; J Appl Physiol; 81(6):2680-2689; Dec. 1996.

Chadha et al.; Validation of respiratory inductive plethysmography using different calibration procedures; Am Rev Respir Dis; 125:644-649; Jun. 1982.

Chen et al.; Color structured light system of chest wall motion measurement for respiratory volume evaluation; J Biomed Opt; 15(2):026013; Mar.-Apr. 2010.

Chourabi et al.; Understanding smart cities: An integrative framework; 45th Hawii International Conference on System Sciences; pp. 2289-2297; Jan. 4, 2012.

D'Angelo et al.; A system for respiratory motion detection using optical fibers embedded into textiles; Conf Proc IEEE Med Biol Soc; 3694-3697; Aug. 2008.

Dodgson; Variation and extrema of human interpupillary distance; Prod. of SPIE: Stereoscopic Displays and Virtual Reality Systems XI; vol. 5291; pp. 36-46; Jan. 2004.

Ferrigno et al.; Three-dimensional optical analysis of chest wall motion; J Appl Physiol; 77(3):1224-1231; Sep. 1994.

Gramse et al.; Novel concept for a noninvasive cardiopulmonary monitor for infants: a pair of pajamas with an integrated sensor module; Ann Biomed Eng; 31(2):152-158; Feb. 2003.

Heilman et al.; Accuracy of the LifeShirt (Vivometrics) in the detection of cardiac rhythms; Biol Psychol; 75(3):300-305; Jul. 2007.

Kenyon et al.; Rib cage mechanics during quiet breathing and exercise in humans; J Appl Physiol; 83(4):1242-1255; Oct. 1997.

Konno et al.; Measurement of the separate volume changes of rib cage and abdomen during breathing; J Appl Physiol; 22(3):407-422; Mar. 1967.

Lafortuna et al.; A new instrument for the measurement of rib cage and abdomen circumference variation in respiration at rest and during exercise; Eur J Appl Physiol Occup Physiol; 71(2-3):259-265; Mar. 1995.

Milledge et al.; Inductive plethysmography—a new respiratory transducer; J Physiol; 267(1):4P-5P; May 1977.

Peacock et al.; Optical mapping of the thoracoabdominal wall; Thorax; 39 (2):93-100; Feb. 1984.

Peacock et al.; Optical measurement of the change in trunk volume with breathing; Bull Eur Physiopathol Respir; 21(2):125-129; Mar.-Apr. 1985.

Pennock B.E.; Rib cage and abdominal piezoelectric film belts to measure ventilatory airflow; J Clin Monit; 6(4):276-283; Oct. 1990.

Purao et al.; Modeling citizen-centric services in smart cities; 32nd. International Conference on Conceptual Modeling; Hong Kong; pp. 438-445; (8 pages, retrieved from the internet at https://icity.smu.edu.sg/sites/icity.smu.edu.sg/files/publications/Modeling-Citizen-centric-Services-in-Smart-Cities_ER2013.pdf); Nov. 11-13, 2013.

Sackner et al.; Calibration of respiratory inductive plethysmograph during natural breathing; J Appl Physiol; 66(1):410-420; Jan. 1989.

Saumarez; Automated optical measurements of human torso surface movements during freathing; J. Appl. Physiol.; 60(2); pp. 702-709; Feb. 1986.

Zimmerman et al.; Postural changes in rib cage and abdominal volume-motion coefficients and their effect on the calibration of a respiratory inductance plethysmograph; Am Rev Respir Dis; 127(2):209-214; Feb. 1983.

(56) References Cited

OTHER PUBLICATIONS

Longinotti-Buitoni et al.; U.S. Appl. No. 15/516,138 entitled "Devices and methods for use with physiological monitoring garments," filed Mar. 31, 2017.
Longinotti-Buitoni et al.; U.S. Appl. No. 15/877,378 entitled "Flexible fabric ribbon connectors for garments with sensors and electronics," filed Jan. 22, 2018.
Longinotti-Buitoni et al.; U.S. Appl. No. 15/905,811, entitled "Physiological monitoring garments with enhanced sensor stabilization," filed Feb. 26, 2018.
Hossain et al.; Human identity verification by using physiological and behavioural biometric traits; International Journal of Bioscience, Biochemistry and bioinformatics; 1(3); pp. 199-205; Sep. 2011.

\* cited by examiner

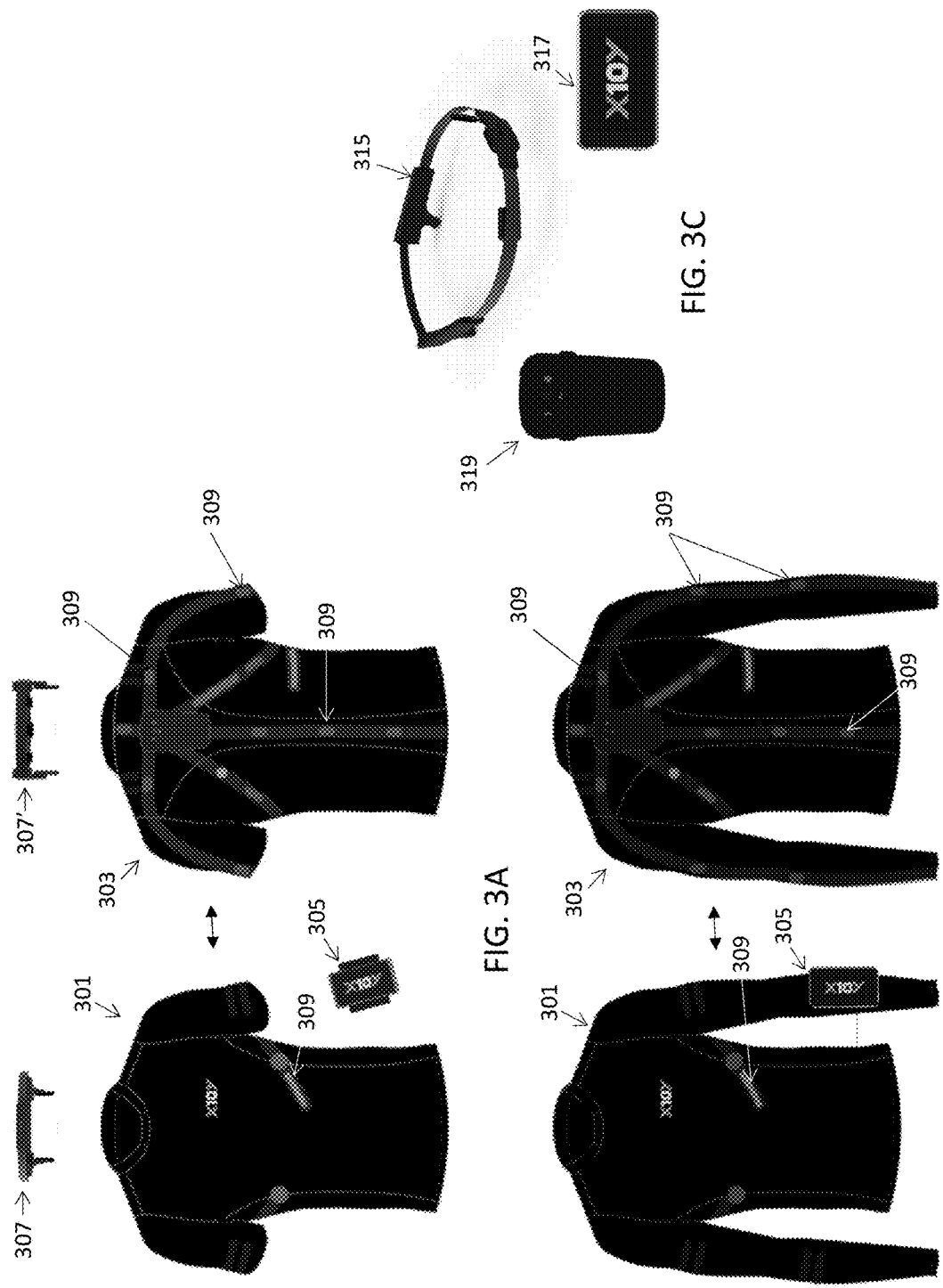

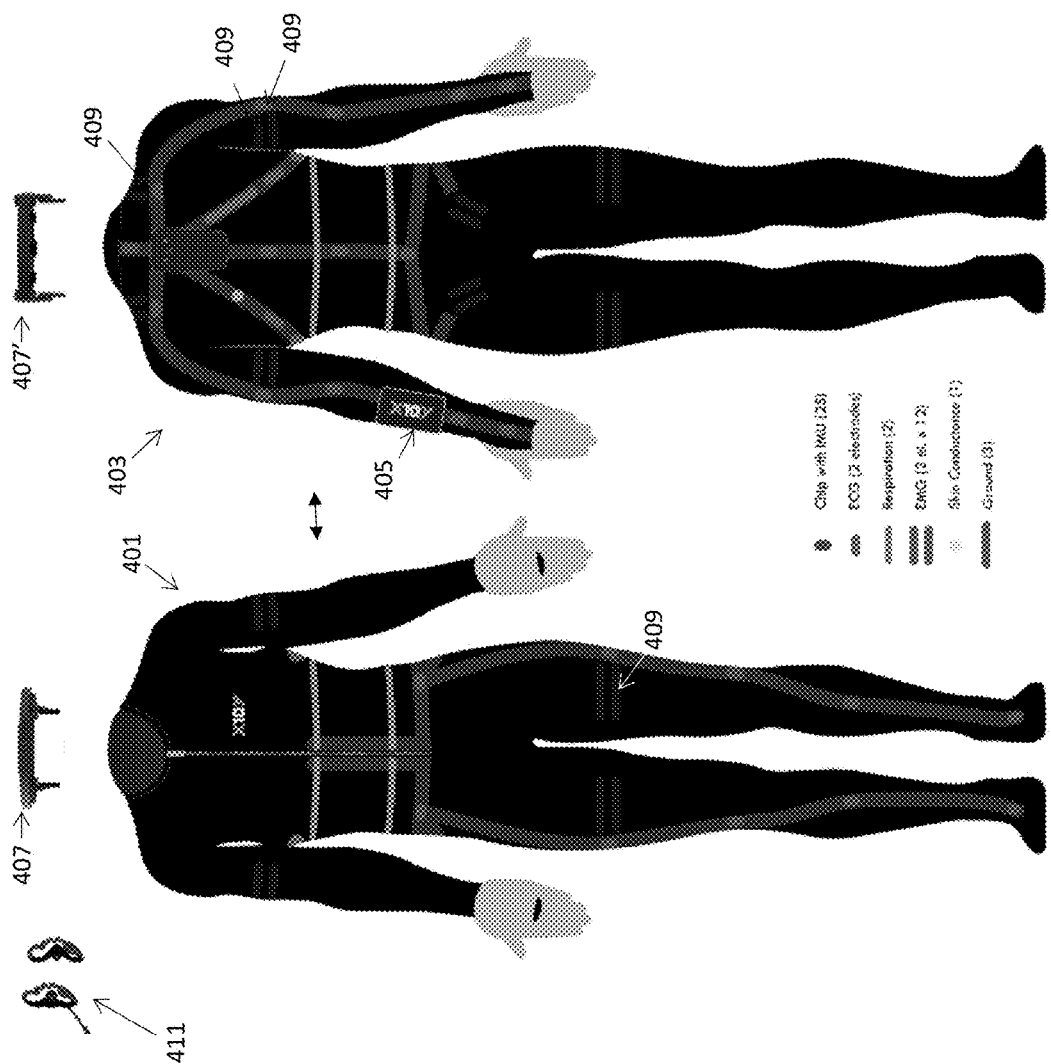

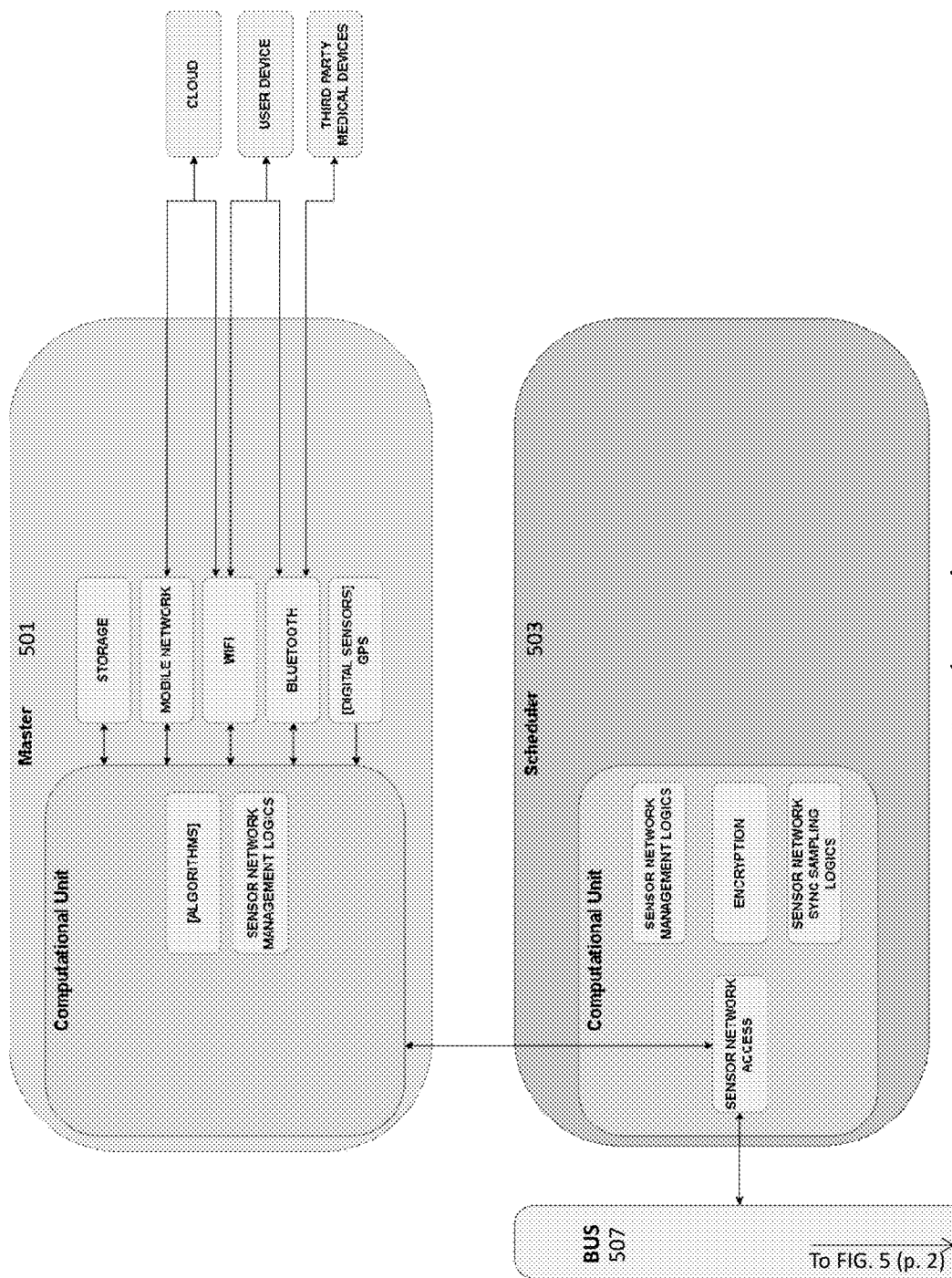
FIG. 5 (part 1)

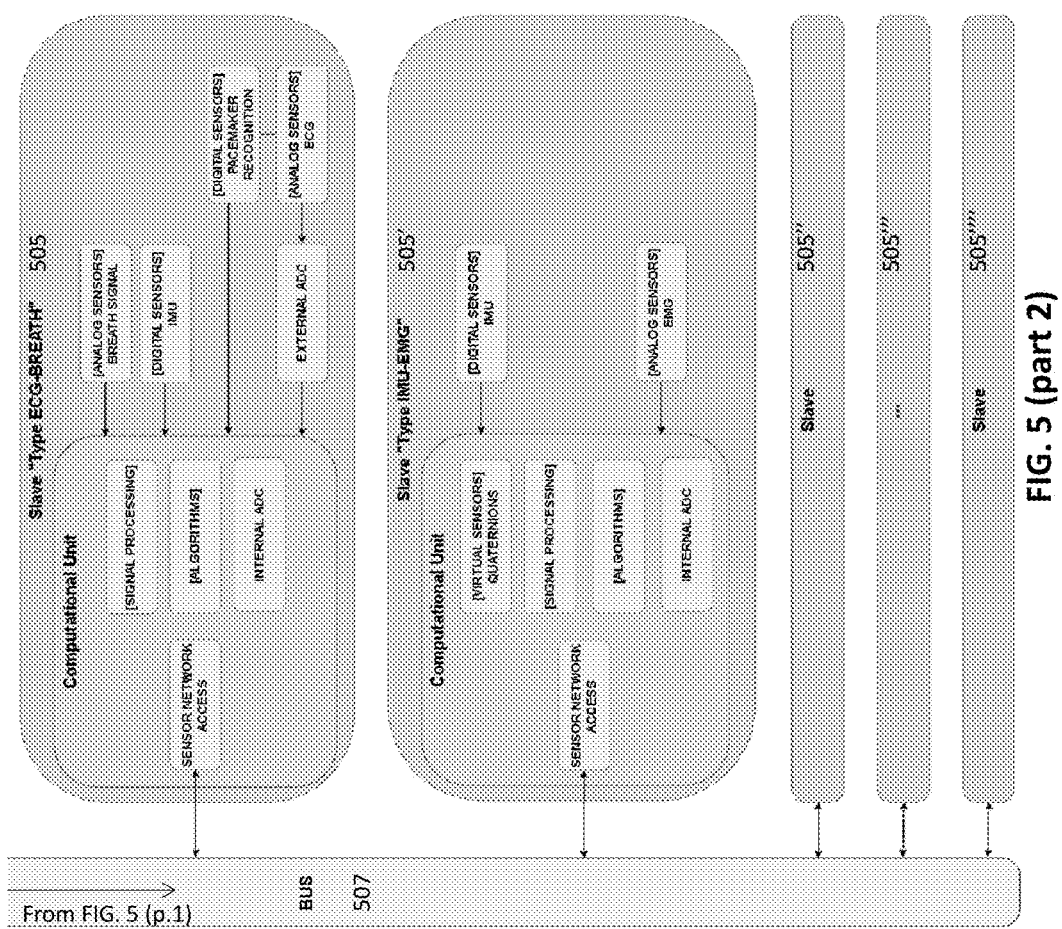
FIG. 5 (part 2)

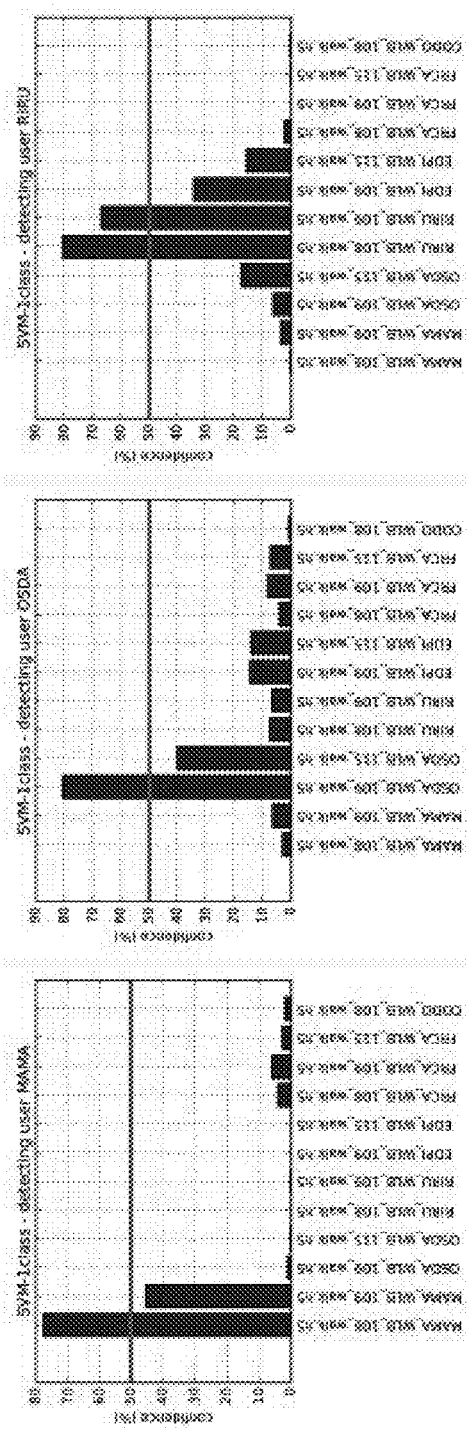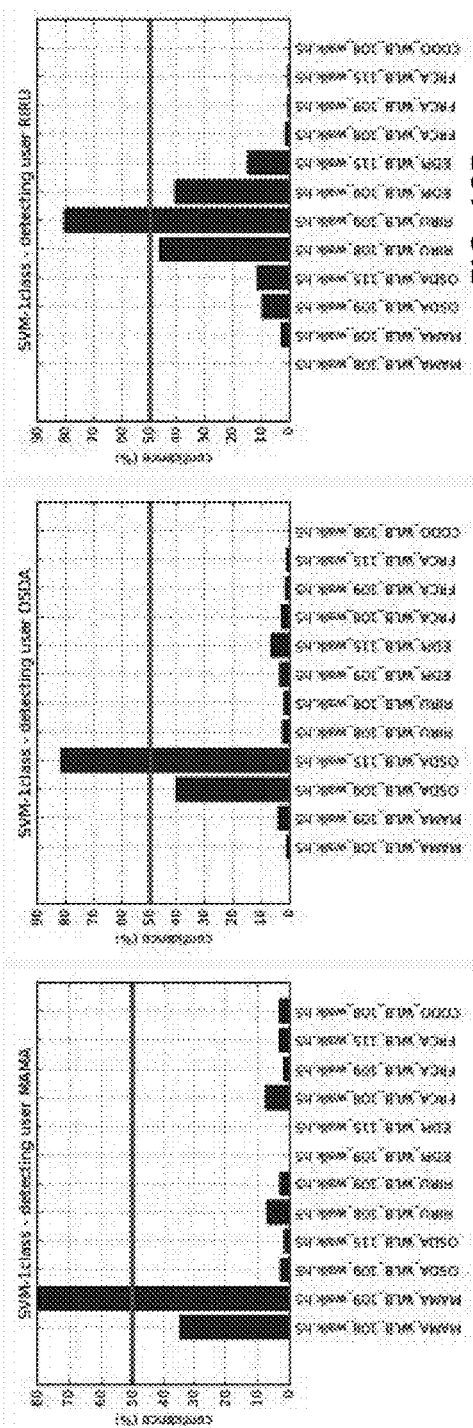

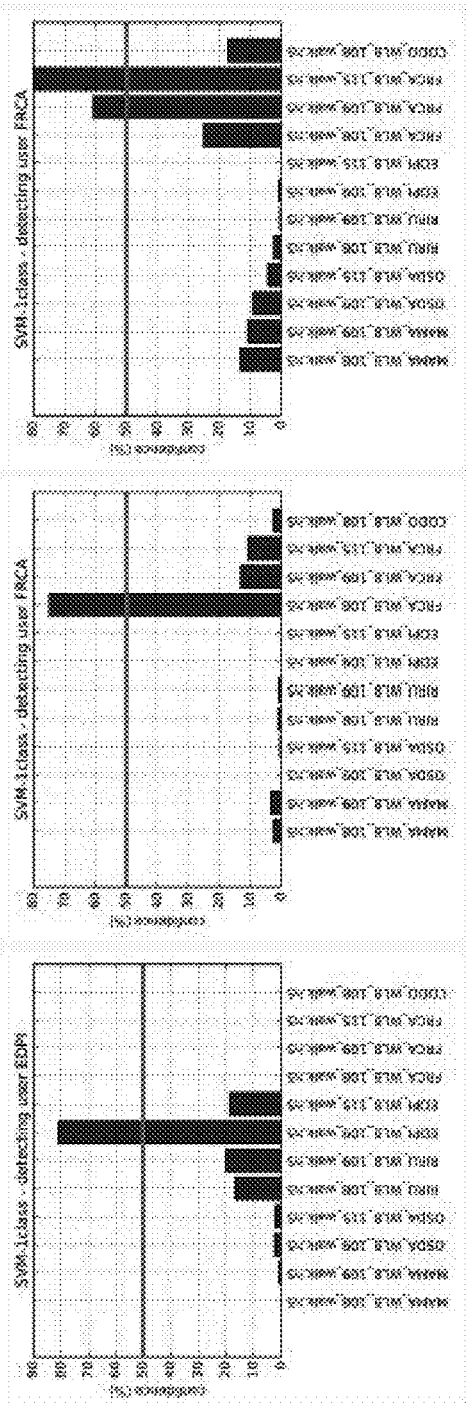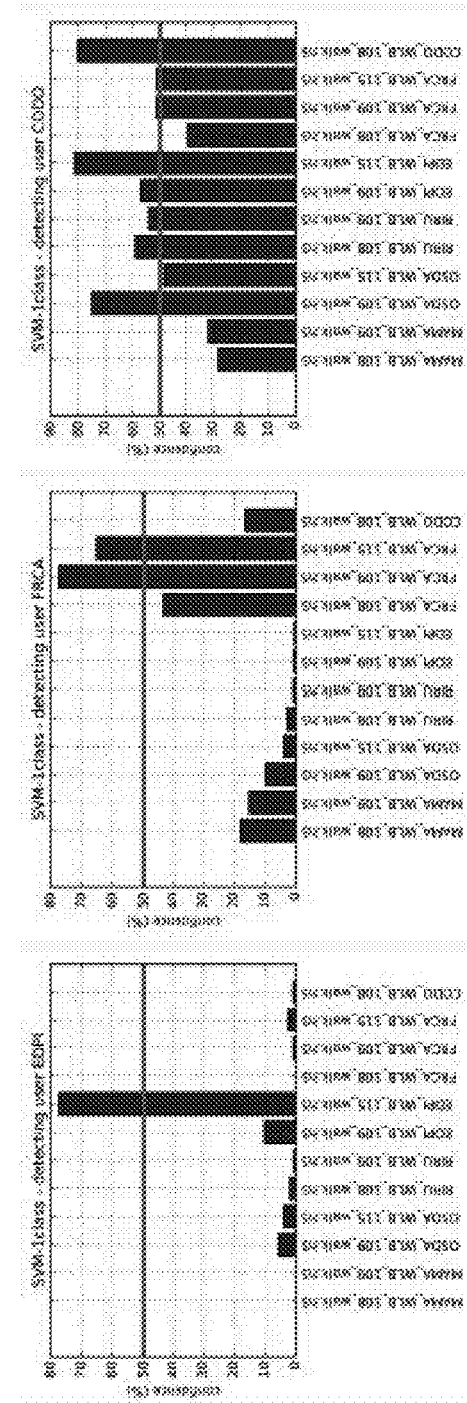

BIOMETRIC IDENTIFICATION BY GARMENTS HAVING A PLURALITY OF SENSORS

CROSS REFERENCE TO RELATED APPLICATIONS

This patent application claims priority to U.S. provisional patent application No. 62/357,665, titled "BIOMETRIC IDENTIFICATION BY WORN MOVEMENT SENSORS," and filed on Jul. 1, 2016, the entirety of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are systems and methods to determine and/or confirm the identity of an individual based on an analysis of sensed parameters from a plurality of sensors worn as part of an integrated garment. The sensors may include a plurality of sensor management subsystems (SMSes) distributed in characteristic positions as part of the garment(s). These SMSes may be coordinated for local sensing, including precise time-coordination with a central processor, and may record a variety of different parameters including, but not limited to individuals body movements, including voluntary movements (e.g., gait, arm, hand, leg, finger, foot, knee, elbow, chest, etc. movements), and involuntary movements or reactions (e.g., respiratory rate, heart rate, ECG, EMG, EOG, etc.), from which a biometric pattern may be determined. The voluntary and involuntary movements or reactions may be linked to the voluntary movements. A biometric indicator may be learned by the system while wearing the apparatus, and features extracted from the recorded data in order to generate a biometric template. The biometric template may be stored and used as a test against future biometric templates (tokens) from the same or different garments worn by the user to uniquely identify the user. Described herein are methods of forming an identifying biometric template, methods of storing and transmitting the biometric template information securely, and/or methods of using the biometric template to uniquely and accurately identify an individual. Also described herein are the apparatuses (devices and systems) performing these methods as well.

For example, described herein are garments having a variety of sensors forming SMSes that may be used to determine, confirm, or analysis biometric identification.

BACKGROUND

It has become increasingly important to uniquely identify an individual. Stealing or hacking personal, financial, medical and security information is increasingly common. Attacks against digital information databases are increasing. For example, by 2015, fraudulent card transactions have exceeded $11 billion a year worldwide, of which the U.S. represents 50%, while Europe follows with 15% of the total. Health insurance providers are one of the many industries most affected by hacking. In 2014, 47% of American adults had their personal information stolen by hackers-primarily through data breaches at large companies. In 2013, 43% of companies had a data breach in which hackers got into their systems to steal information. Data breaches targeting consumer information are on the rise, increasing 62% from 2012 to 2013, with 594% more identities stolen. Data about more than 120 million people has been compromised in more than 1,100 separate breaches at organizations handling protected health data since 2009. The data reflects a staggering number of times individuals have been affected by breaches at organizations trusted with sensitive health information.

Some of the data can be used to pursue traditional financial crimes, such as setting up fraudulent lines of credit, but it can also be used for medical insurance fraud, including purchasing medical equipment for resale or obtaining pricey medical care for another person. Personal information is also at risk, including information about an individual's mental health or HIV treatments.

Existing solutions are not adequate. For example, the security of passwords (e.g., password-protected systems) depends on a variety of factors. Compromising attacks, such as protection against computer viruses, man-in-the-middle attacks (where the attacker secretly intrudes into the communication of two unaware parties intercepting their conversation), physical breech (such as bystanders steeling the password by covertly observing thorough video cameras, e.g., at ATMs machines), etc. The stronger the password, the more secure is the information it protects. Strength may be a function of length, complexity and unpredictability. Using strong passwords lowers overall risk of a security breach, but strong passwords do not replace the need for other effective security controls. The effectiveness of a password of a given strength is strongly determined by the design and implementation of the factors (knowledge, ownership, inherence).

Tokens (security tokens) are used to prove one's identity electronically, as in the case of a customer trying to access their bank account. The token is used in addition to or in place of a password to prove that the customer is who they claim to be. The token acts like an electronic key to access something.

The simplest vulnerability with any password container is theft or loss of the device. The chances of this happening, or happening unawares, can be reduced with physical security measures such as locks, electronic leashes, or body sensors and alarms. Stolen tokens can be made useless by using two factor authentication. Commonly, in order to authenticate, a personal identification number (PIN) must be entered along with the information provided by the token the same time as the output of the token.

Any system which allows users to authenticate via an untrusted network (such as the Internet) is vulnerable to man-in-the-middle attacks. In this type of attack, a fraudulent party acts as the "go-between" the user and the legitimate system, soliciting the token output from the legitimate user and then supplying it to the authentication system themselves. Since the token value is mathematically correct, the authentication succeeds and the party is improperly granted access.

Trusted as much a regular hand-written signature, a digital signature should ideally be made with a private key known only to the person authorized to make the signature. Tokens that allow secure on-board generation and storage of private keys enable secure digital signatures, and can also be used for user authentication, as the private key also serves as a proof for the user's identity.

For tokens to identify the user, all tokens must have some kind of number that is unique. Not all approaches fully qualify as digital signatures according to some national laws. Tokens with no on-board keyboard or another user interface cannot be used in some signing scenarios, such as confirming a bank transaction based on the bank account number that the funds are to be transferred to.

Biometrics (e.g., biometric identification systems) often physical features to check a person's identity, ensure much greater security than password and number systems. Biometric features such as the face or a fingerprint can be stored on a microchip in a credit card, for example. A single feature, however, sometimes fails to be exact enough for identification. Another disadvantage of using only one feature is that the chosen feature is not always readable.

A template protection scheme with provable security and acceptable recognition performance has thus far remained elusive. Development of such a scheme is crucial as biometric systems are beginning to proliferate into the core physical and information infrastructure of our society. Described herein are methods and apparatuses that may address the issues discussed above.

SUMMARY OF THE DISCLOSURE

Described herein are apparatuses (systems, methods, including garments, etc.) and methods that allow individual owners to use their identifier, which may be based on a wearable (e.g., garment) capable of medical-level physiological data and biometrics measuring, acting as a communication platform, which may allow a user to uniquely identify herself/himself in order to perform security-sensitive actions such as being identified, generating medical data, transferring funds, purchasing goods, modify contracts, enter in restricted—access areas, etc., with certainty of identity, without divulging data to a third party, minimizing the risk of data being stolen. These methods and apparatuses may convert data detected in a predefined manner from any of the wearable apparatuses described herein (or similar in at least some of the functional characterisitcs described herein) into biometric template information that may be stored and later compared against other similarly-acquired biometric information to confirm a user's identity. This information may act as a token in a security protocol, method or system. These methods and apparatuses may generate the biometric information from one or more wearable garments including a plurality of integrated SMSes; the garment may securely receive, record and transmit a biometic template or token derived from the one sensor (or more likely plurality of sensors) integrated into the garment (s), in minimal time and with minimal cost. A biometric may be a measurement of a physiological trait, traditionally such as fingerprint, iris pattern, retina image, hand or face geometry, or it can be a behavioral trait such as voice, body sweating, gait. Current biometric technology identifies individuals automatically through one or several of these traits. Automatically means that the person's trait has been scanned, converted into a digital form in a database or on identity card. Thus current technology obliges individuals to divulge their data (to the database that will identify them) with the risk of the database being hacked or the card being stolen. The moment users divulge their data they have lost it, potentially irrevocably: unlike passwords, biometrics cannot be easily changed. Furthermore current biometric technology may not be accurate because it is not able to be universally present, unique to the individual, stable over time and easily measurable and have the disadvantage that, unlike a password, a person's characteristics are not secret and can therefore be copied. Once copied biometric data is lost forever: unlike a password it cannot be reset. The methods and apparatuses (e.g., systems and devices) described herein may overcome these limitations. See, e.g., U.S. Pat. No. 6,016,476, describing a portable information and transaction processing system and method utilizing biometric authorization and digital certificate security.

Commonly used biometric traits include fingerprint, face, iris, hand geometry, voice, palmprint, handwritten signatures, and gait. Biometric traits have a number of desirable properties with respect to their use as an authentication token, namely, reliability, convenience, universality, and so forth. These characteristics have led to the widespread deployment of biometric authentication systems. But there are still some issues concerning the security of biometric recognition systems that need to be addressed in order to ensure the integrity and public acceptance of these systems. There are five 5 major components in a generic biometric authentication system, namely, 1) sensor, 2) feature extractor, 3) template database, 4) matcher, and 5) decision module. 1) Sensor is the interface between the user and the authentication system and its function is to scan the biometric trait of the user. 2) Feature extraction module processes the scanned biometric data to extract the salient information (feature set) that is useful in distinguishing between different users. In some cases, the feature extractor is preceded by a 2A) quality assessment module which determines whether the scanned biometric trait is of sufficient quality for further processing.

The systems described herein may not need all of these components, since biometric data may are not necessarily stored in a database; instead these systems may use data generate during the biometric identification process. Thus, these systems may not need a template database. Otherwise, during enrollment, the extracted feature set may be stored in a database as a template (XT) indexed by the user's identity information. Since the template database could be geographically distributed and contain millions of records (e.g., in a national identification system), maintaining its security is often not a trivial task. The matcher module is usually an executable program, which accepts two biometric feature sets XT and XQ (from template and query, resp.) as inputs, and outputs a match score (S) indicating the similarity between the two sets. Finally, the 5) decision module makes the identity decision and initiates a response to the query.

A fish-bone model can be used to summarize the various causes of biometric system vulnerability. At the highest level, the failure modes of a biometric system can be categorized into two classes: intrinsic failure and failure due to an adversary attack. Intrinsic failures occur due to inherent limitations in the 1) sensing, 2) feature extraction, or 3) matching technologies as well as the 4) limited discriminability of the specific biometric trait. In adversary attacks, a resourceful hacker (or possibly an organized group) attempts to circumvent the biometric system for personal gains. We further classify the adversary attacks into three types based on factors that enable an adversary to compromise the system security. These factors include system administration, nonsecure infrastructure, and biometric overtness.

Intrinsic failure is the security lapse due to an incorrect decision made by the biometric system. A biometric verification system can make two types of errors in decision making, namely, 1) false accept and 2) false reject. A genuine (legitimate) user may be falsely rejected by the biometric system due to the large differences in the user's stored template and query biometric feature sets. These intra-user variations may be due to incorrect interaction by the user with the biometric system (e.g., changes in pose and expression in a face image) or due to the noise introduced at the sensor (e.g., residual prints left on a fingerprint sensor). False accepts are usually caused by lack of individuality or uniqueness in the biometric trait which can lead to large similarity between feature sets of different users (e.g., similarity in the face images of twins or siblings). Both intrauser variations and interuser similarity may also be caused by the use of nonsalient features and nonrobust matchers. Sometimes, a sensor may fail to acquire the biometric trait of a user due to limits of the sensing technology or adverse environmental conditions. For example, a fingerprint sensor may not be able to capture a good quality fingerprint of dry/wet fingers. This leads to failure-to-enroll (FTE) or failure-to-acquire (FTA) errors. Intrinsic failures can occur even when there is no explicit effort by an adversary to circumvent the system. So this type of failure is also known as zero-effort attack. It poses a serious threat if the false accept and false reject probabilities are high. Ongoing research is directed at reducing the probability of intrinsic failure, mainly through the design of new sensors that can acquire the biometric traits of an individual in a more reliable, convenient, and secure manner, the development of invariant representation schemes and robust and efficient matching algorithms, and use of multibiometric systems The apparatuses and methods described herein may allow one to build a measuring systems that can reduce or eliminate the risk of incorrect decisions being made by the biometric system by synthesizing a large variety (e.g., large array) of biometic data (e.g., specifying which, why and how) provided by the apparatus/garment acting as a biometric system and/or communications platform.

The methods and apparatuses described herein may provide biometric security that may possess the following four properties. Diversity: the secure template must not allow cross-matching across databases, thereby ensuring the user's privacy. Revocability: it should be straightforward to revoke a compromised template and reissue a new one based on the same biometric data. Security: it must be computationally hard to obtain the original biometric template from the secure template. This property prevents an adversary from creating a physical spoof of the biometric trait from a stolen template. Performance: the biometric template protection scheme should not degrade the recognition performance (FAR and FRR) of the biometric system.

Typically, biometric recognition is probabilistic; it is not an absolutely accurate and certain identification technology and, according to critics, this is one of the technology's key limitations. In other words, biometric systems will always only provide a probability of verification. There have been moves to manage the probabilistic nature of biometric matching and the challenges that this represents, for example by introducing 'multi-modal biometrics' such that the uniqueness of a match (i.e. the likelihood of making a correct match) increases with the number of biometrics that are combined (i.e. whilst it is likely that someone might have a fingerprint pattern that matches yours, it is far less likely that someone will have both a fingerprint and an iris image which match yours). In other words: the fusion of multiple biometrics helps to minimise the system error rates.

However, the use of multi-modal biometric systems then entails a different set of limitations and challenges. First, multi-modal biometrics is more expensive as it requires more data to be collected and processed. Besides that, another challenge confronting the implementation of multi-modal biometric systems is that a crucial question still remains unresolved; namely the question of what are the best combinations (modalities). Moreover, multi-modal biometric systems are also challenging to implement because of the complexities involved in making decisions "about the processing architecture to be employed in designing the multi-modal biometric system as it depends upon the application and the choice of the source. Processing is generally complex in terms of memory and or computations." Besides that, there are also still a number of unresolved issues about the scalability of multi-modal biometric systems. Finally, increasing the amount of biometrics being collected from an individual might increase the performance of the system but might also, at the same time, increase the risk of data theft or misuse of individual information.

Biometrics can be defined as "any automatically measurable, robust and distinctive physical characteristic or personal trait that can be used to identify an individual or verify the claimed identity of an individual." Contemporary biometric technologies may entail the digitalization of the unique body part, a process that has implications for the knowledge produced from the processing of this digitalized biometric data and hence for the body subjected to this technology, in particular given the possible political use of such biometrically-derived knowledge.

Described herein are systems that through a wearable apparatus (e.g., a wearable computing & communicating device that covers a significant part of the user's body, e.g., one o more of: torso, arms, legs; and may also include one or more of: head, hands, feet, etc.) accurately measures a plurality of biometrical data (using the same or multiple modalities) to generate an accurate identification of a person, in a private (no third party intrusion), automatic (directly executed by the computing and communication module thus sidestepping user intervention that could generate errors), simple (identification is activated by a single input such as a voice command, a touch on the garment, such as a touch point, a smart screen touch, etc.), fast (synthesis can be produced in just a few seconds), repeatable (it can be generated as many times as needed), low cost (e.g., virtually no execution cost to the owner of apparatus) and controlled manner (the user is in control and needs no external support). The apparatus may generate its owner identity: a synthesis of traits and data that make her/him unmistakably who she/he is. Most importantly, the system allows the person to be the sole owner of the identification data produced. Present biometric-recognition systems require sharing data with a database owned by a third party (government, medical facility, financial institution, vendor, etc.) in order for the person to be identified. Being identified through biometrics today has a substantial cost to the data owners of data: they lose ownership of their data and possibility to generate and income with it. In today ever more digital economy, data is becoming exponentially more valuable: the value is today collected by large corporations rather than by their natural/legitimate owners, partly a cause of today vast economic divide. Securing ownership of personal data could be a mean to close the divide gap by allowing owners to monetize their ever more valuable data.

The biometric identification apparatuses described herein may be: universal, i.e., each individual possesses this characteristic; easily measured, i.e., it is quite easy technically and convenient for an individual to obtain the characteristic; unique, i.e., there are no two individuals with identical characteristics; and permanent, i.e., the characteristic does not change over time.

Ideally the characteristic should be universally present, unique to the individual, stable over time and easily measurable. No biometric characteristics have been formally proven to be unique, although they are usually sufficiently distinct for practical uses. Different biometrics will be more suitable for different applications depending, for example, on whether the aim is to identify someone with their co-operation or from a distance without their knowledge.

For example, described herein are methods of confirming a user's identity using a garment including a variety of sensors. For example, the method may include: wearing a garment comprising a plurality of integrated sensors at predetermined locations; synchronously recording sensor data from multiple predetermined locations on the garment; generating, in the garment, a biometric token from the recorded sensor data; transmitting the biometric token to a lodger in or on the garment; and transmitting the biometric token to a third party having a biometric template against which the biometric token may be tested.

Generating a biometric token from the recorded sensor data may comprise generating the biometric token in a master and/or scheduler on the garment. The master and/or scheduler may include a processor.

Wearing may include adjusting the position of the sensors based on haptic feedback from the garment. For example, the garment may include one or more haptics that will vibrate or otherwise indicate that a nearby sensor in the garment is not properly positioned on the user's body.

Synchronously recording sensor data may comprise synchronously recording sensor data from a plurality of motion sensors. The sensors may be of different types (e.g., different modes, such as respiration sensors, cardiac sensors, galvanic skin sensors, EMG sensors, EEG sensors, etc.). Synchronously recording sensor data may comprise synchronously recording sensor data from a plurality of motion sensors, one or more respiration sensors and one or more electrodes configured to contact the user's skin when the garment is worn. Wearing the garment may comprise wearing the garment over the user's torso (e.g., the garment may be a shirt, or may include a shirt). Synchronously recording may include synchronously recording sensor data from multiple sensor types on the garment. For example, the scheduler and/or master may coordinate the recording of sensor (slave) data; each sensor or sub-sets of sensors may record at different frequencies based on the type of sensor it is. Thus, synchronously recording sensor data may comprise recording data at a plurality of frequencies.

Any of these methods may also include encrypting the biometric token prior to transmitting the biometric token to the third party. Thus, in general, the biometric token is determined using the master and/or scheduler, which may also encrypt the biometric token.

Since the user may wear the apparatus (garment with sensors) continuously for a long period of time, the biometric token may be determined on an ongoing basis (e.g., a running window) and/or upon demand (e.g., upon a request for identity verification).

Any of the methods and apparatuses described herein may also include encrypting and transmitting the biometric template that can be used by a third party to compare with the biometric token. For example, the garments described herein may generate a biometric template upon some triggering event 9 e.g, wearing the garment for a predetermined time) or upon request from a third party.

The substance of the biometric template and/or biometric token, including the type of data (sensor type, etc.) may be determined, for example, based on the ability of that type of data to distinguish identity of the individual wearing the garment. For example, the biometric template may be constructed from accelerometer data (including from one of the axes of motion of the accelerometer, such as one axis of motion of the accelerometer) and/or recorded electrical activity (e.g., cardiac data, EMG data, galvanic skin response data, etc.) and/or respiration data.

Any of these methods may also include sending a coded message requesting approval of the wearer to proceed from the third party. An approval message may be transmitted to the user in a coded (e.g., in a Morse-like tactile code), and a response code may be transmitted by responding to specific location on the garment (e.g., tactile output) and/or to a touchscreen in communication with the device. Thus, contacting an output on the garment may be used to indicate agreement to the third party.

For example, a method of confirming a user's identity may include: wearing a garment comprising a plurality of integrated sensors at predetermined locations in the garment that are configured to position the integrated sensors over the user's torso; synchronously recording sensor data from multiple predetermined locations on the garment, using a plurality of different sensor types; generating, in the garment, a biometric token from the recorded sensor data; and transmitting the biometric token to a third party having a biometric template against which the biometric token may be tested.

A method of confirming a user's identity may include: wearing a garment comprising a plurality of integrated sensors at predetermined locations in the garment that are configured to position the integrated sensors over the user's torso; adjusting the position of the sensors using haptic feedback from the garment; synchronously recording sensor data from multiple predetermined locations on the garment, using a plurality of different sensor types; generating, in the garment, a biometric token from the recorded sensor data; encrypting the biometric token; and transmitting the encrypted biometric token to a third party having a biometric template against which the biometric token may be tested.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3A-3C illustrate another example of a garment for determining a biometric token or template, configured as a performance/fitness garment.

FIGS. 4A-4B illustrate another example of a garment for determining a biometric token or template.

FIG. 5 is an example of a schematic for a general apparatus (e.g., system) for determining biometric template/token information.

FIGS. 10A-10F illustrate detection confidence for three users in a sparse dataset.

FIGS. 11A-11F illustrate detection confidence for three users in a sparse dataset in an alternative embodiment.

DETAILED DESCRIPTION

Described herein are biometric identification methods and apparatuses (including devices and systems) for uniquely identifying one an individual based on a garment including one (or more preferably a plurality) of sensors, including but not limited to sensors having multiple sensing modalities (e.g., movement, respiratory movements, heart rate, ECG, EEG, etc.).

Figure 1:
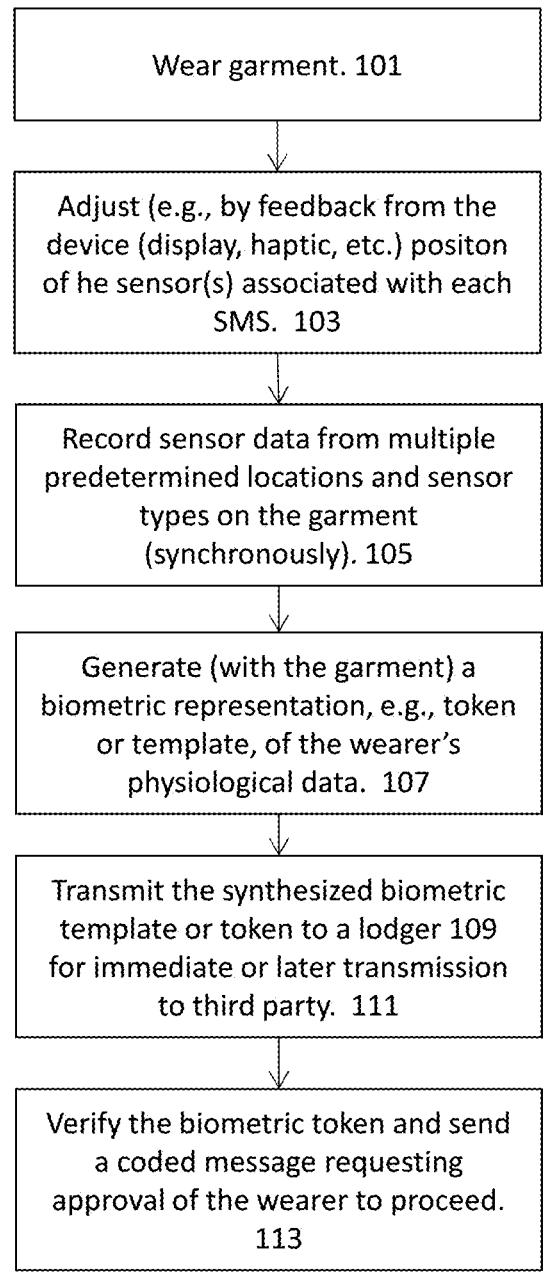
FIG. 1 is a schematic illustrating one example of a method of using a garment having a plurality of sensors to generate a unique biometric code (e.g., token or template).

FIG. 1A illustrates an exemplary sequence of operations to produce the identity synthesis. This sequence may be part of a method (or in an apparatus as software, hardware and/or firmware configured to control the apparatus to generate a biometric token or template that may uniquely identify a user with a very high degree of certitude.

In the first step 101, the user (also referred to as a subject or wearer) may wear the device. In general, the device may be a garment including a plurality of SMSes that each receive and/or record, and/or process sensor data from one or more sensors. For example, the apparatus may be a garment such as the garments described in one or more of U.S. patent application Ser. No. 14/023,830, titled "WEARABLE COMMUNICATION PLATFORM" (Now U.S. Pat. No. 9,282,893); U.S. patent application Ser. No. 14/331,142, titled "COMPRESSION GARMETS HAVING STRETCHABLE AND CONDUCTIVE INK" (Now U.S. Pat. No. 8,948,839); U.S. patent application Ser. No. 14/612,060, titled "GARMENTS HAVING STRETCHABLE AND CONDUCTIVE INK" (US-2015-0143601-A1); U.S. patent application Ser. No. 14/331,185, titled "METHODS OF MAKING GARMENTS HAVING STRETCHABLE AND CONDUCTIVE INK" (Now U.S. Pat. No. 8,945,328; U.S. patent application Ser. No. 15/324,152, titled "GARMENTS HAVING STRETCHABLE AND CONDUCTIVE INK"; U.S. patent application Ser. No. 15/202,833, titled "SYSTEMS AND METHODS TO AUTOMATICALLY DETERMINE GARMENT FIT" (US-2016-0314576-A1); U.S. patent application Ser. No. 14/644,180, titled "PHYSIOLOGICAL MONITORING GARMENTS" (US-2015-0250420-A1); U.S. patent application Ser. No. 15/516,138, titled "DEVICES AND METHODS FOR USE WITH PHYSIOLOGICAL MONITORING GARMENTS"; and U.S. patent application Ser. No. 15/335,403, titled "CALIBRATION PACKAGING APPARATUSES FOR PHYSIOLOGICAL MONITORING GARMENTS," each of which is herein incorporated by reference in its entirety.

These apparatuses (e.g., garments) may include a tutorial application to ensure that the device is properly worn and a) all the sensors are properly functioning and/or correctly positioned. Alternatively or in addition, when wearing the garment, the processor (e.g., computer) communicating with or integrated into the apparatus may detect that a sensor is not working and may indicate it on the smartscreen (e.g., touchscreen), and/or by haptic feedback near the sensor 103. For example, a message indicating that the sensor needs to be positioned or worn correctly/adjusted may appear on the smart phone or computer's screen in communication with or integrated into the garment.

In general, sensors integrated into the garment(s) may be properly positioned in the right place. For example: IMU need to be positioned in the middle of the segment (shoulder to elbow, elbow to wrist), on the back of the hand between wrist and knuckles.

Once worn and adjusted, the device may be worn for a few minutes or longer so that sensors adapt to body temperature.

The apparatus may then activate the production of synthesis of biometric data from the plurality of sensors (e.g., from the plurality of SMSes). For example, the apparatus may be activated automatically or manually, e.g., through a touch point (touching a microchip on the sleeve for example), through voice command, a sensorial command or other type of command. Thereafter, the apparatus may produce a biometric representation (e.g., token or template) of the wearer's physiological data 107. This is described in greater detail below, and generally includes collecting sensor data, e.g., from coordinated SMSes on/in the garment and analyzing the data in an ongoing or discrete manner to evaluate one or more characteristics ("prototypes") specific to each sensor (per characteristic sensor type and location). The biometric representation may be perfected through machine learning. Thus, the more the owner uses the device, the more precise the identity synthesis algorithm becomes.

The method and biometric representation can also be made more accurate by using more than one garment or a garment covering more than one region. For example, the garment may be a garment configured to collect medical diagnostic information. the wearer may wear the garment that covers the body from the tip of the toes (leggings incorporating socks) to the top of the head/balaclava see, e.g., FIG. 2.

Figure 2:
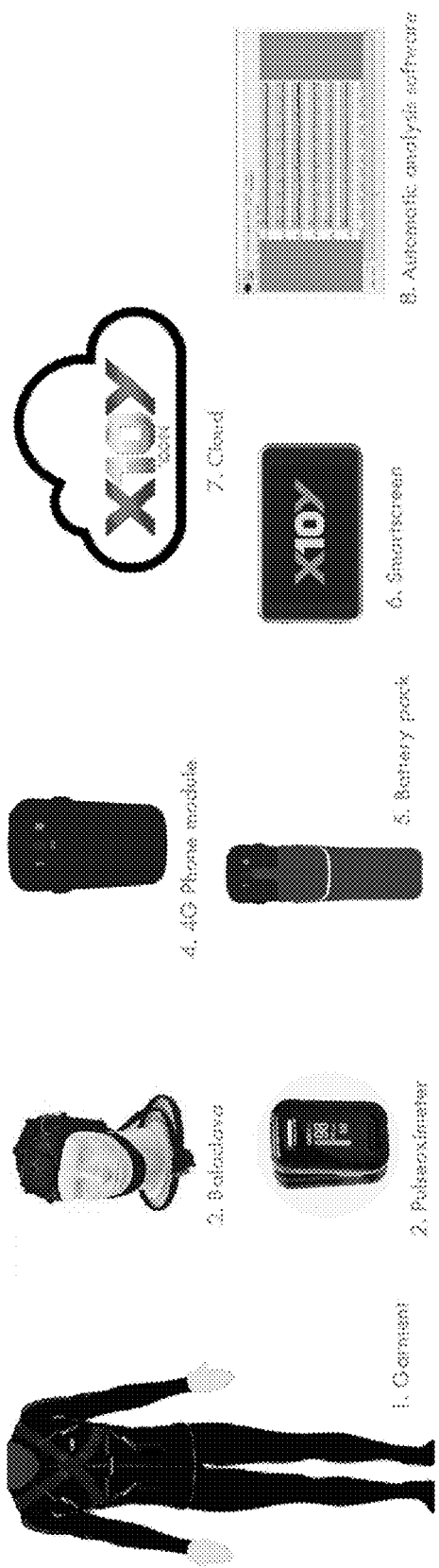
FIG. 2 is an example of an apparatus (e.g., system) comprising a garment for measuring a biometric token or template, configured for medical monitoring.

The apparatus in FIG. 2 is an exemplary system that includes a bodysuit/garment 1 a headpiece 2, an optional pulse oximeter sub-subsystem 3, a controller (e.g., phone module) 4, an optional battery pack 5, a touchscreen display 6, a remote server (e.g., cloud) 7, and automatic analysis software 8, which may execute on the remote server and/or on the controller. This apparatus can provide many hours of a very large array of physiological data recording through a long period of time (from a few hours to 100 hours plus with auxiliary batteries). This exemplary apparatus may be used from 12 to 48 hours (e.g., while sleeping and in daily activity) once a week or once a month.

The system shown in FIG. 2 may monitor, for example, respiratory mechanics, PSG, e.g.,: thoracic and abdominal movements, sleep patterns, oxygen saturation (including the time course of oxygen saturation in different body regions under different activity conditions), ECG measurements (e.g., via an integrated Holter 12 lead ECG sensors). Any of these garments may also include a plurality of movement sensors, such as accelerometers at predetermined positions on the body, secured in reproducible relation to the body by the garment.

Other garments covering more or less of the body may be used. For example, a garment configured as an efficiency device that may monitor and provide feedback to the owner during daily life to improve health by, for example, analyzing activities and improving habits, may also be used. This apparatus may be, for example, an upper-body device with short or long sleeves very comfortable to be worn during daily life and may optionally include a visor or glasses to monitor EEG, EOG, EMG facial signals, body temperature, and one or more IMUs to monitor head movements, etc. See, e.g., FIGS. 3A-3C. FIG. 3A shows another variation of a wearable sensing garment having a plurality of sensors 309 on the front 301 and back 303 of the garment. The garment may be worn with a touchscreen 305 at or near the wrist/forearm of the wearer. A collar unit 307 may include a speaker and one or more microphones (e.g., for voice recognition, etc.). The variation show in FIG. 3A is a short-sleeved garment. A similar long-sleeved variation is shown in FIG. 3B. Additional (and optional) accessory such as headband/neckband 315, smartphone 317 and battery pack 319 are shown in FIG. 3C. The sensors shown may include electrodes for measuring galvanic skin responses, movement (e.g., 9 or more IMUs), electrodes for measuring electrocardiograms (ECGs), electrodes for measuring EMGs, and ground electrode(s).

Other garments may also include an apparatus configured as a performance device that supports the owner during regular or intensive fitness activities or professional sports. See, e.g., FIGS. 4A (front 301) and 4B (back 303) of an exemplary garment. In this example, the garment also includes a plurality of sensors 409 (e.g., galvanic skin responses, movement (e.g., 9 or more IMUs), electrodes for measuring electrocardiograms (ECGs), electrodes for measuring EMGs, and ground electrodes, etc.). The garment may also include a collar 405, 405' and speakers (shown as earpieces 411). The optional components shown in FIG. 3C may also be used with the garment of FIG. 4A-4B.

By wearing any of these garments for a period of time (e.g., 1 day, 1 week, 2 or more weeks, 1 month, or more months, etc.) for short period of time (e.g., with the medical device garment of FIG. 2, e.g., once a week, with the garment of FIG. 3A-3C, every day for a few hours, with the performance/fitness garment, 2 to 3 times a week), the apparatus may develop a knowledge of the heart at a medical diagnostic ECG level even when using the apparatus despite the fact that it only has, e.g., 2 sensors rather than the 12 derivations.

Physiological data captured by the many sensors may be processed in multiple locations throughout the body. For example, the sensors (e.g., IMUs or EMGs) may be positioned in proximity of an SMS (e.g., microchip) that process the data. The physiological data may be jointly processed into the Sensor Management System (SMS). Thus, the data may be synchronously processed at multiple locations in the garment 105; the different processors may be synchronized and the data accurately time stamped (e.g., to within +/−1 ms, 0.1 ms, 0.001 ms, etc.). The synchronized data are processed/calculated with minimal latency, and may be recombined and/or further processed. SMS software and/or firmware can calculate data at different Hertz velocities depending on the type of physiological data. For example IMU may be measured at 500 Hertz, heart rate at the same or at a different frequency (e.g., 100 Hz or less), respiration at the same or at a different frequency (e.g., 10 Hz), EEG at the same or at a different frequency (e.g., 200 Hz), EOG at the same or at a different frequency (e.g., 300 Hz), EMG at the same or at a different frequency, Skin conductance at the same or at a different frequency, body temperature at the same or at a different frequency, etc.

In general, any of the methods and apparatuses described herein may include tactile feedback, via one or more haptic actuators (e.g., piezoelectric actuators, etc.). For example, the devices may be equipped with haptic actuators to provide touch feedback at or near the sensor(s). Haptic feedback may be provided when confirming that the sensor(s) are correctly positioned. Haptic actuators may provide a tactile feedback to the user to indicate that the synthesis has been performed by the SMS. The synthesis may include the formation of a biometric template or token that is synthesized from a plurality of different sensors or combination of sensors in/on the garment. Once synthetized, the biometric template or token may be encrypted. For example, the synthesis of the biometric template/token may be an encrypted 532 to 1064 characters in SMS.

The synthesized biometric template or token may then be sent by a lodger 109 (a telecommunications module, such as a cell phone or wireless-enabled unit that may be located in or on the garment, e.g., on the upper-back between the shoulder blades in a torso garment such as a shirt). The biometric template or token may be sent to an interested party 111 that may verify the biometric token and then send a coded message requesting approval of the wearer to proceed, assuming that the biometrics match 113. The request for approval may be displayed on the garment, including on a display integrated into or in communication with the garment. Approval may be provided by a touchpoint in/on the garment and/or a touchscreen. For example, in case of a bank access, before approval of a payment, the biometric information may be transmitted from the garment (lodger) to the bank, acting as the third party. Assuming that the bank has a reference biometric template to compare to (which is also encoded), the bank may verify the biometric information from the garment and may then request additional verification. Additional (optional) security may then be provided; for example, the coded message may be delivered on the garment by haptic actuators in a Morse-type code chosen by the user. The user may then send approval to the bank. In some variations, the synthesis can be stored in a blockchain.

In general, the garments described herein may include a sensor network (e.g., a network of sensor elements, including a master, a scheduler, and one or more slaves (sensors). The slave(s) may be the last element(s) of the sensor network, and may typically be placed directly on the garment. More than one slave sensor can be attached to the sensor network. As mentioned, the garment may support more than one sensor. The slaves/sensors may be responsible to: directly acquire data from sensors, execute signal processing, execute algorithms, derive virtual sensor data from hardware sensors (e.g., Quaternions), etc.

Different sensor types supported. For example, slave breath sensors (e.g., "Type ECG-BREATH") may be configured to acquire data from a 12-lead ECG and breathing sensors. Slave motion sensors (e.g., "Type IMU-EMG") may be configured to acquire data from an IMU (e.g., Accelerometer, Gyroscope, Magnetometer, Quaternions) and/or EMG sensors.

A scheduler may be placed inside of a control device or directly on/in a garment. The scheduler may generally manage the sensor network of the garment, and may organize slaves to execute synchronous sampling. The scheduler may control and synchronize the clocks in the individual regions of the garment (and may include a master clock, and may coordinate the sample frequencies and/or synchronize the sensors). The scheduler may also encrypt data provided to the master, and/or provide the access of the sensor network to the master. The scheduler may include circuitry (e.g., clock, processor, memory, etc.).

A master may also be included in the control device, and may be configured to manage the sensor network (e.g., thorough the scheduler). The master may obtain data from the sensor network (e.g., encrypted by the scheduler), and may execute control logic (e.g. processes) and/or may directly acquire data from the sensors, store data, exchange data with a remote server (e.g., the cloud, for example, through WiFi/mobile network), exchange data with an external user device (e.g., through WiFi/Bluetooth), and/or exchange data with an external third party medical devices (e.g., through Bluetooth).

FIG. 5 is a schematic overview of an apparatus (configured as a system in this example) as described. In FIG. 5, the master 501 communicates directly with the scheduler 503, while the scheduler communicates with the plurality of sensors (slave 505, 505', 505", 505'", etc.) in the garment through a bus 507.

In some variations, the biometric apparatuses described herein are wearable devices that cover the major part of the body to maximize the number of sensors located around the body; in general, the higher the number of sensor the higher the medical accuracy of the data. This may also help to ensure that sensors are located in the best possible part of the body for maximum precision. A sensor located around the heart may be more precise then a sensor on the wrist (like in wearable bracelets and watches). The device may be comfortable (e.g., preventing data noise distortions introduced by constriction/lack of comfort), and can be used during daily life (generating more relevant data and habits far from the anxieties and risks of hospitals and medical laboratories) for long period of time. Longer measurement times may enhance the chance to discover pathologies or abnormalities in garments configured for medical use, and may also provide greater accuracy for the data through machine learning.

The apparatuses described herein may not need a password to authenticate an individual, which may substantially increasing the ease of use. Passwords may get misplaced or are forgotten. The biometric technologies linked to the particular individual such as those described herein may provide greater security, speed, and ease of use than traditional methods like passwords, PIN's, or "smart" cards. Biometric login can also save time and reduce costs.

Rather than simply generate physiological data to compare to previously stored physiological data bases, the methods and apparatuses described herein may determine reliable biometric templates from sensors in/or a garment, these biometric templates may be generalizable between different garments. This may reduce the risk of the user's physiological data being held in possession of a third party (e.g., such as the US government as currently done for fingerprints and retinal scans). The systems, devices and methods described herein may help ensure that the persons generating the physiological data remains the sole owner of their data and does not need to divulge their data in order to be identified or in order to use their data to make transactions or to monetize it.

Thus, in general, the validation server does not store sensitive user data such as personally identifiable information (PII). A user's unique biometric signature may remain within trusted execution and may not ever be transmitted over the web. Raw biometric data may never be sent through the network or stored in a central database.

The systems described herein may replaces and compete with existing tokens. These systems are typically a synthesis of users' physiological data. The methods and apparatuses described do not reveal the owner's physiological data, but merely provide extracted and/or calibrated information that may be further processed.

Advantageously, the use of multiple, synchronized sensors as described herein may allow for rapid and robust sensing. For example, the apparatuses described herein may generate an accurate biometric token within under about 10 seconds. Typically these systems may only works with the owner of the system. Once the system is worn for more than a few times (e.g., more than 5 times, more than 6 time, more than 7 times, more than 8 times, more than 9 times, more than 10 times, etc.) it may recognizes its owner and may be configured to only works when it is worn by the owner.

As mentioned, any combination of different physiological data types may be used. for example, at least 3 types of physiological data (e.g., at least four types, at least five times, at least six types, etc.) may be used to generate an accurate synthesis of the biometric template/token. For example, heart, respiration, movement, and rest (EEG, EOG, EMG, temperature, skin conductance, etc.), or any component part of these. For example, an accelerometer may include three different axes (x, y, z), which may be analyzed separately or together.

In any of these variations, SMS information may be encrypted so that data is protected before being sent. The data may be encrypted before being passed into the phone module to guarantee safety. Once a transaction is automatically approved by a third party device after comparing the biometric template based on a wearable garment with sensors stored by the third party with a biometric token based on a wearable garment with sensors, a message may be sent to the wearable garment's haptic system of the wearer/owner of physiological data. The haptic communication may be a 'pass-haptic signals' in a Morse-type code rather than a 'password' and thus it can be reset.

The signal may be performed by two different haptic actuators placed in two different parts of the body, which may oblige the owner to wear the device properly.

The data may be saved in a physiological data platform (e.g., in the cloud or in a secure remote server. The authentication may be given by the physiological data platform after matching the data. A biometric encryption may help ensure that a user's credentials are decentralized and stored offline. A cryptographic digital key may be generated from a biometric such as a fingerprint or voice and used to sign transactions initiated by a relying party. Raw biometric data may not be sent through the network or stored in a central database.

Thus, the authentication solutions described herein may provide biometric encryption without requiring an authentication channel relying on a centralized storage of biometrics. End-users may be able to choose which biometric authenticators they will utilize. Biometric data may remain encrypted and protected against malware on a user's device. Relying parties set policies for which biometric authenticators can be used. A UAF Server may provide the server side of UAF protocols; HYPR makes it easy to deploy any FIDO server on-premises or as a cloud solution.

Using public key cryptography, it is possible to prove possession of a private key without revealing that key. The authentication server may encrypt a challenge (typically a random number, or at least data with some random parts) with a public key; the device describe described herein may allow the apparatus to prove it possesses a copy of the matching private key by providing the decrypted challenge.

Figure 12:
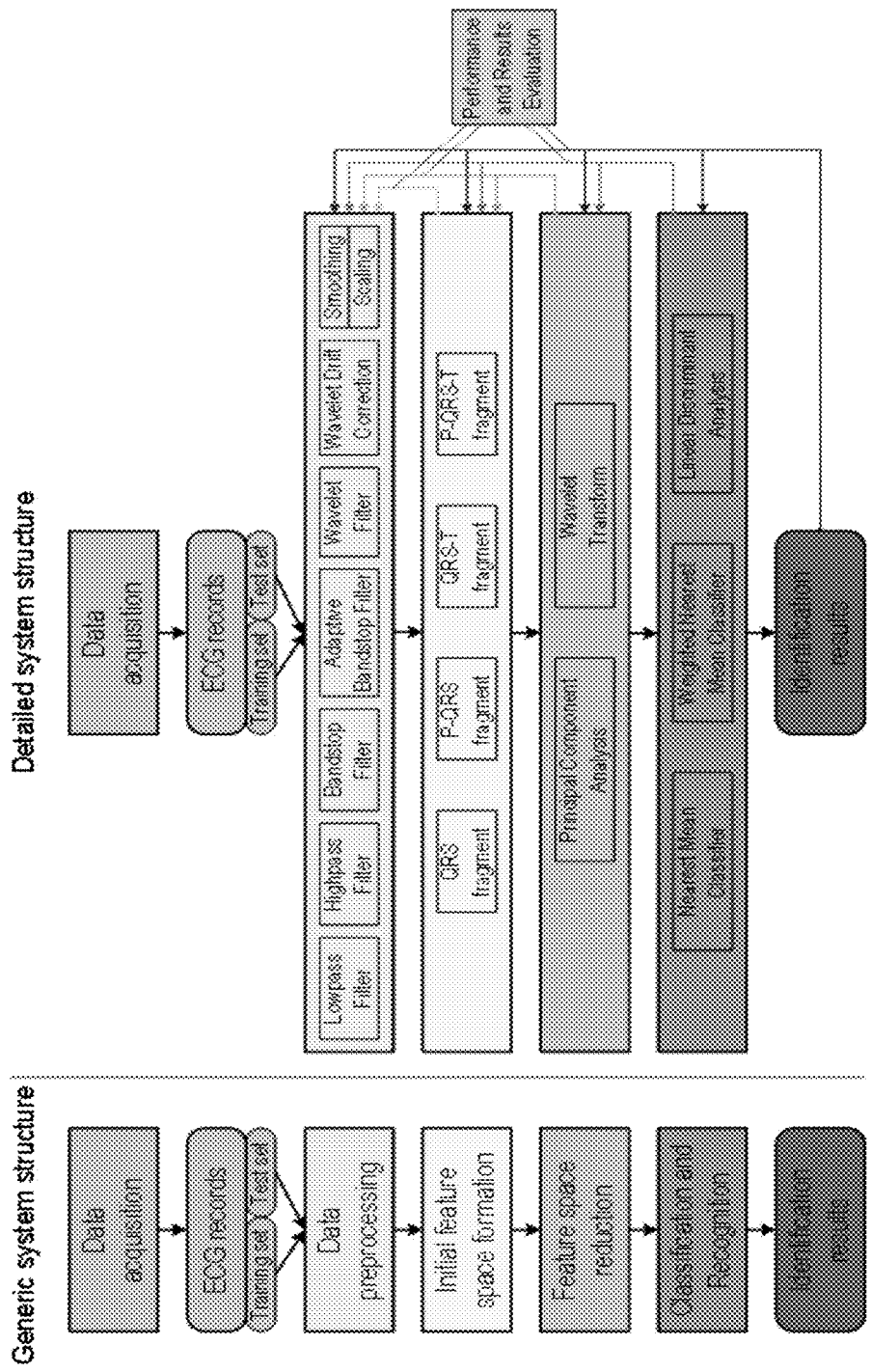
FIG. 12 is a generic biometric data system as described herein.

The identification systems described herein may use a classical scheme including data acquisition, data preprocessing, formation of input feature space, transition to reduced feature space, and sensor information classification. The generic system structure (FIG. 12, left) shows the sequence of essential data processing stages. Feed forward links show processed data transfer between stages. The output of one stage is the input to the subsequent stage. Each stage can be implemented using different processing methods. The detailed system structure (FIG. 12, right) shows methods considered in this study for each system stage. For most stages, these methods are alternatives, but the data preprocessing stage is usually comprised of several complementary methods.

EXAMPLES

Previously described biometric authentication has typically been based on data derived from direct measurements of a part of the human body, like the DNA, fingerprint, retina, iris, face, ear, palm, the veins' pattern in the hand or in the wrist, etc. The heart activity has also been used for the person authentication, whether by capturing the electrical activity (ECG) or the sound produced by it (PCG). Photoplethysmography (PPG) has also been used for authentication. Vein patterns have also been used. In addition, it is also possible to perform biometric authentication based on behavioral characteristics of the user, which may be linked/coordinated by these physiological responses. For instance, gait, the way the user walks, signature and voice recognition, keystroke-based or by capturing the response of the user (e.g., EEG) to a given stimulus.

Typically, the raw signals captured from direct measurements of the user to be authenticated are characterized and authentication may be based on a comparison between the features of those measurements and the features of the signals measured on the candidate person. For instance, fingerprint authentication may be based on three basic patterns of fingerprint ridges: arches, loops, and whorls. The features or data points defining the authenticated user can define a region or a set of regions in a high-dimensional space. In this case, the procedure of authentication consists on computing if the candidate data lies inside those regions.

Described herein are garments that may provide sufficient biometric information (on both voluntary and involuntary responses) to accurately and reliably be used as biometric identifying data; these garments may further be configured to securely determine from the biometric information a synthesis of biometric templates or tokens that may be used to verify identity of an individual wearing the garment.

Figure 6:
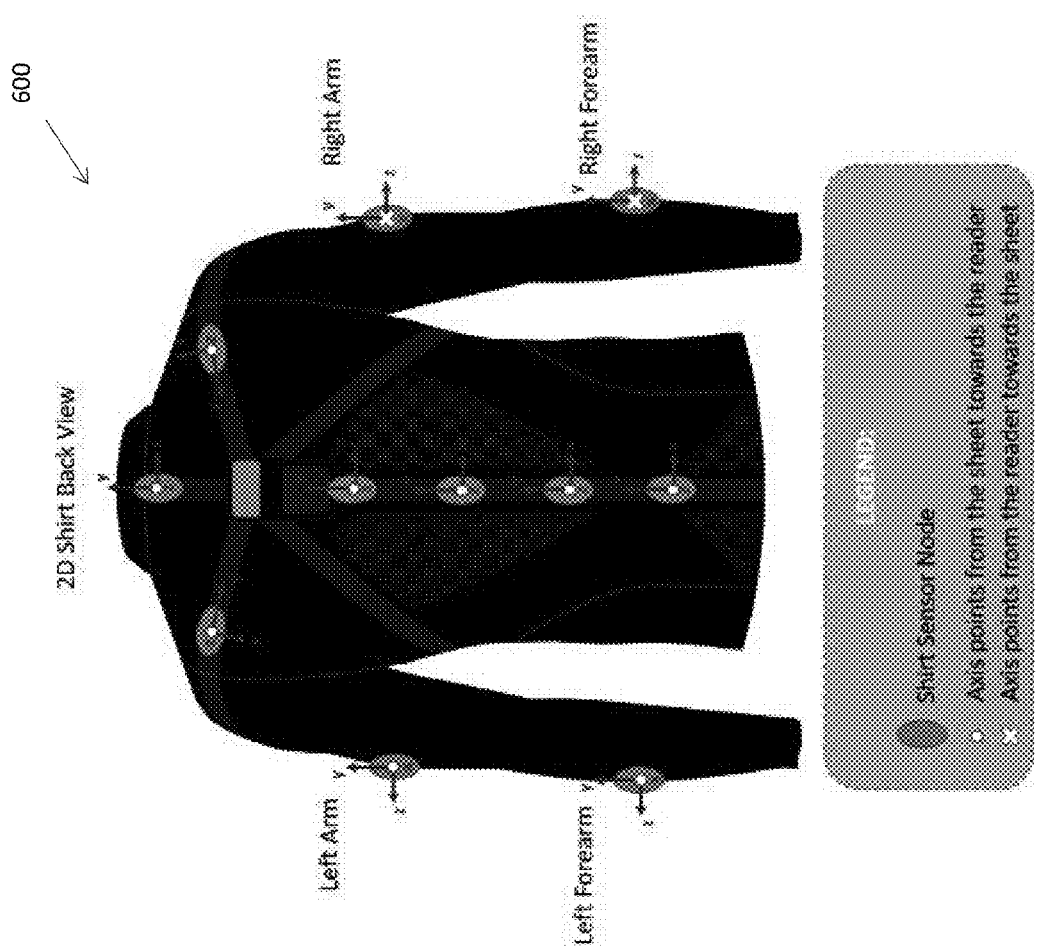
FIG. 6 is an example of a garment 600 including IMU units integrating a 3D-accelerometer, a 3D-gyroscope and a 3D-magnetometer, ECG sensors, breathing sensors, skin-conductance and temperature sensors. This garment may be further configured to determine a biometric template or token based on this sensor information.

FIG. 6 is an example of a garment 600 including IMU units integrating a 3D-accelerometer, a 3D-gyroscope and a 3D-magnetometer, ECG sensors, breathing sensors, skin-conductance and temperature sensors. The garment in FIG. 6 illustrates one possible positioning of these sensors.

In a proof of concept test, multiple IMU units present in the sample garment of FIG. 6 were examined for authentication. In particular, we used the accelerometer. In initial test, the accelerometer data was more reliable than the gyroscope data and the magnetometer was somewhat susceptible to interferences from the environment and dependent on the orientation of the user. In practice, any or all of these sensors may be used. For example, the heart rate signal was, in preliminary data, somewhat noisy; however, the possibility remains for using the breath pattern and the exploitation of multiple modalities.

Initial tests identified sets of signal patterns that are uniquely present in a given individual. The resulting authentication system would be of a behavioral type, given that those signals are generated, for instance while the user is walking and working.

In a first approach, we exhaustively extracted all 1-second time-series of each axis of the available sensors (i.e., 5 sensors×3 axes of acceleration, thus 15 axes). We then proceeded to group those time-series such that for many similar time-series patterns, we chose one single prototype (e.g., by means of a time-series clustering technique such as K-medoids). The user's behavior is thus characterized by a set of prototypes for each sensor axis (in our experiments, 15 sensor axes×50 time-series prototypes). Those 750 prototypes may be different for every user, or that at least, we can base the authentication of a user on the distance between the measured time-series patterns of the candidate user and the prototype time-series characterizing the authenticated user. Thus, the candidate user may be recognized as the authenticated user, if the aforementioned distance is below a certain threshold. The set of prototypes used for characterizing the behavior of a user can be identified whether by a semi-supervised approach or in a completely unsupervised way. Results of this approach are summarized in FIGS. 7A-7C.

In a second approach, we analyzed if a user's way of behaving had a particular pattern in the frequency domain, captured by the IMU's accelerometers. We considered for this purpose all of the available accelerometers in all of the walking datasets. We then computed the power spectrum of the signal for each accelerometer in each of the 3 axes and kept the median signal over periods of 1 minute. We chose a resolution of 0.25 Hz in the frequency domain ranging from 0 to 20 Hz. These median spectra were used to construct a baseline (or prototype) for each specific user. We considered for this purpose a method called Support Vector Data Description (SVDD). This method relies on the construction of a multidimensional domain around typical data points of the target user. The domain is created using a recorded dataset and can then be used to classify new measurements as belonging to the target user or not. Data points falling within the boundaries of the domain are considered as belonging to the user and points falling outside are considered outliers. Therefore, by counting the proportion of points that fall in the domain with respect to the total number of measurements, we can estimate quantitatively the likelihood of the garment being worn by a specific user. Results are presented in FIGS. 8A-8C and 9A-9C.

Figure 7A:
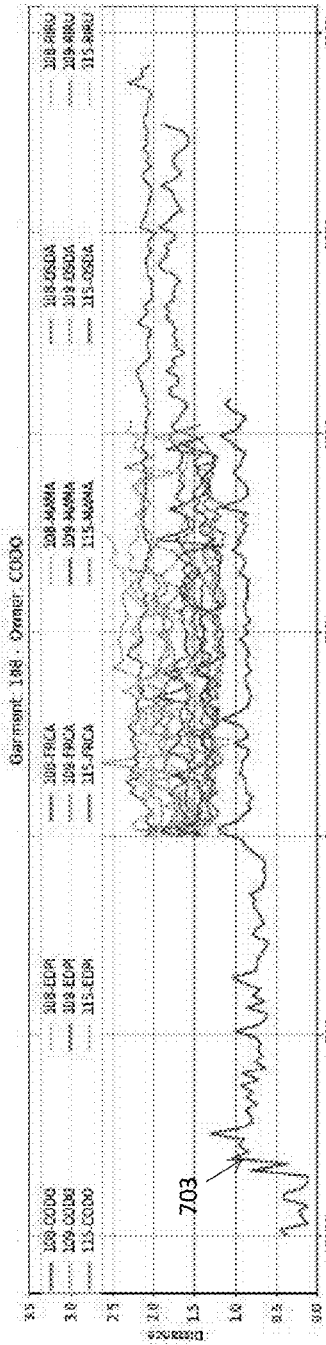
FIGS. 7A-7C illustrate data from a prototypes (such as the one shown in FIG. 6) used for characterizing the behavior of a user can be identified whether by a semi-supervised approach or in a completely unsupervised way.
Figure 7B:
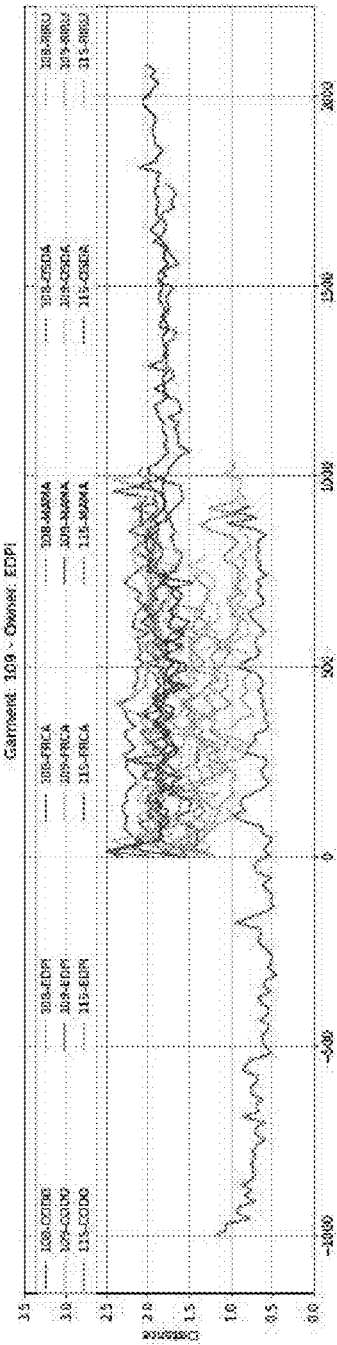
Figure 7C:
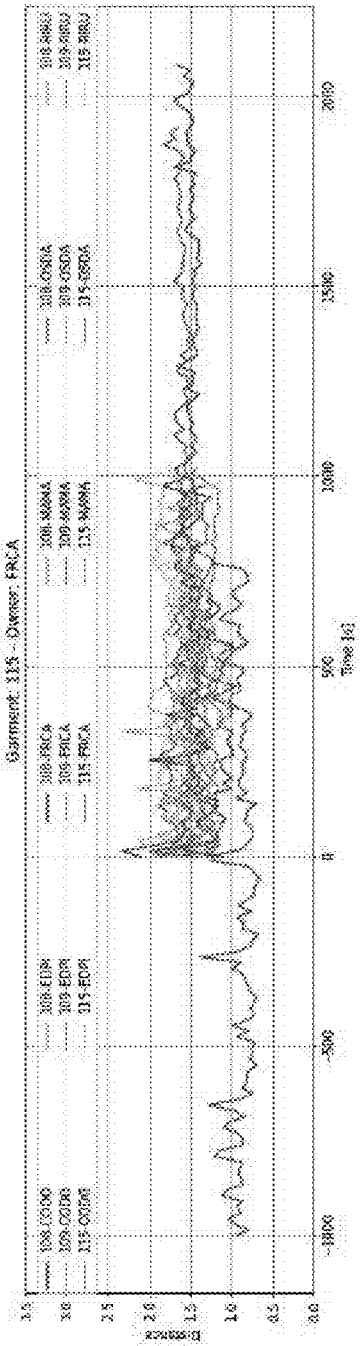

A first approach was to look at time-series clustering. The three plots in FIGS. 7A-7C show the distances between the prototypes of three of the users and the rest of users. For the sake of exemplification consider FIG. 7A. This plot shows the resulting distances when the sequences coming from user COCO wearing the garment 108 were used for building the codebook of prototypes. Hence, the blue curve represents the distances between the prototypes of user COCO-108 and the sequences from the same user. Points before time=0 correspond to training observations. The rest of the curves are the distances between the prototypes of user COCO-108 and the sequences coming from other users (see the labels in the plot). We can say that the first approach effectively discriminate users in this particular setup since the distances represented by the bottom 703 curve (authenticated user) are lower than the distances represented by the other curves (not authenticated users). The same analysis applies for the second and third row (user EDPI with garment 109 and user FRCA with garment 115).

Moreover, we have tested how the distances changed depending on which sensors are used. On the one hand, FIGS. 7A-7C show the resulting distances when all the sensors axis are used. In order to obtain a single value of distances, the distances of each axis are combined by using a weighted average in which each signal is modulated by the compactness of the clusters it generates.

Figure 8A:
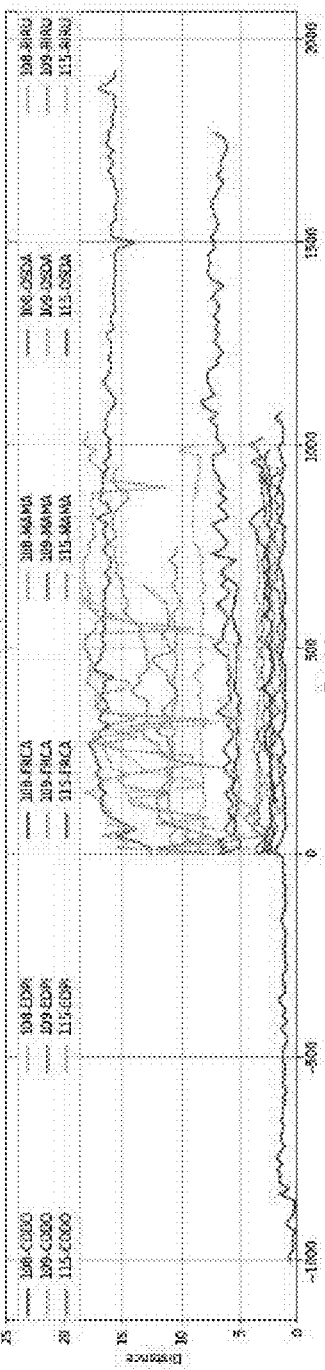
FIGS. 8A-8C illustrate the results of a Support Vector Data Description (SVDD) approach, that relies on the construction of a multidimensional domain around typical data points of the target user to identify biometric data upon which to base (at least in part) a biometric template or token.
Figure 8B:
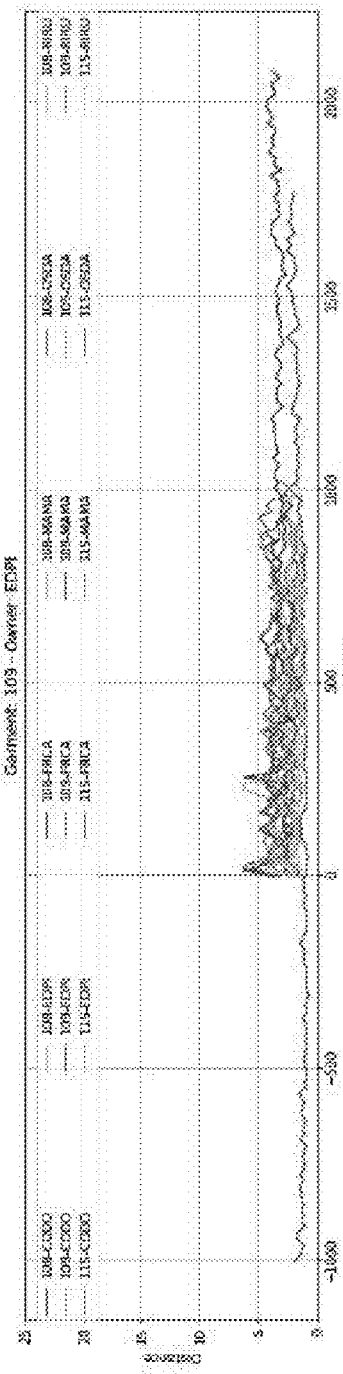
Figure 8C:
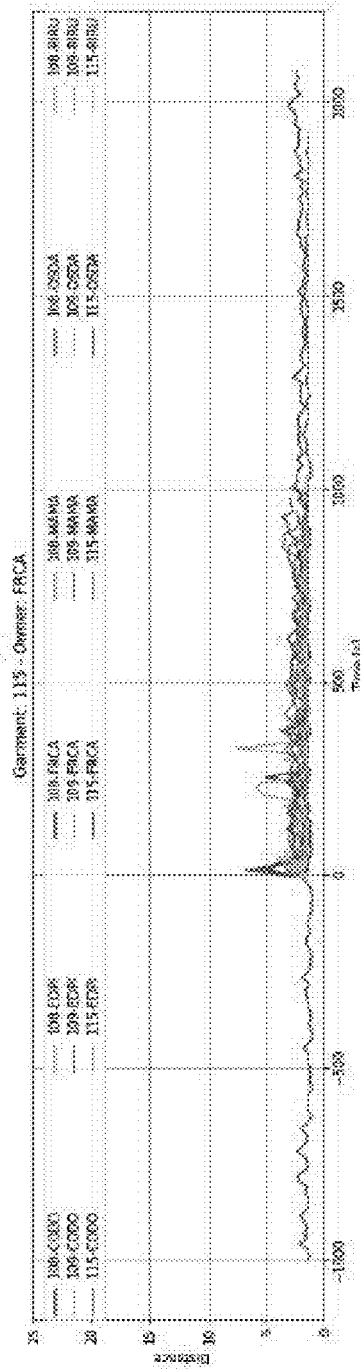
Figure 9A:
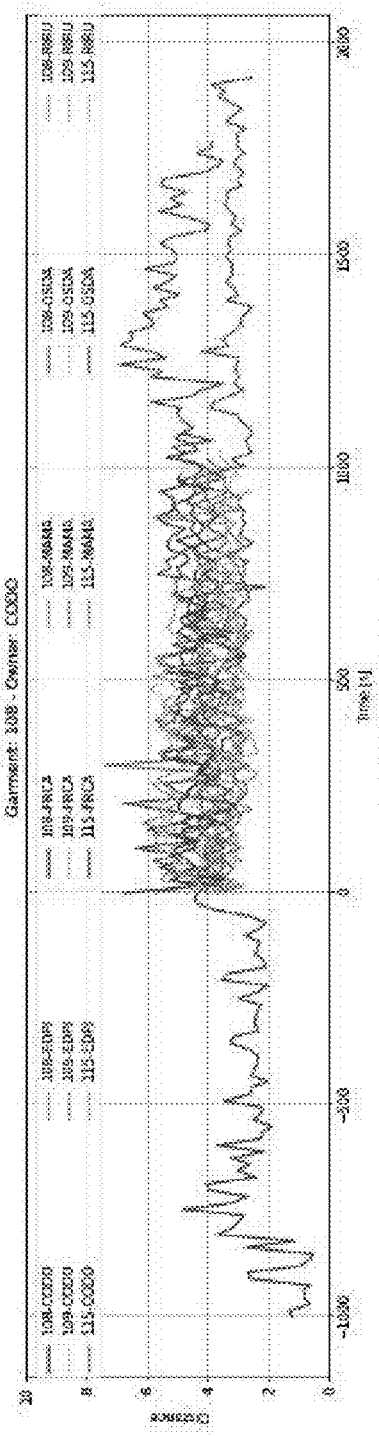
FIGS. 9A-9C are similar to FIGS. 8A-8C, but illustrate a method of approach using the 'worst' feature.
Figure 9B:
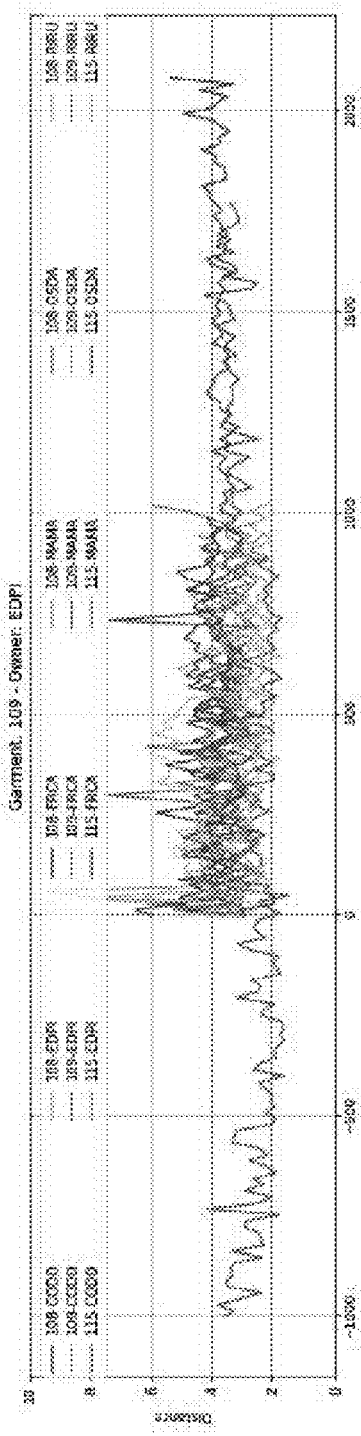
Figure 9C:
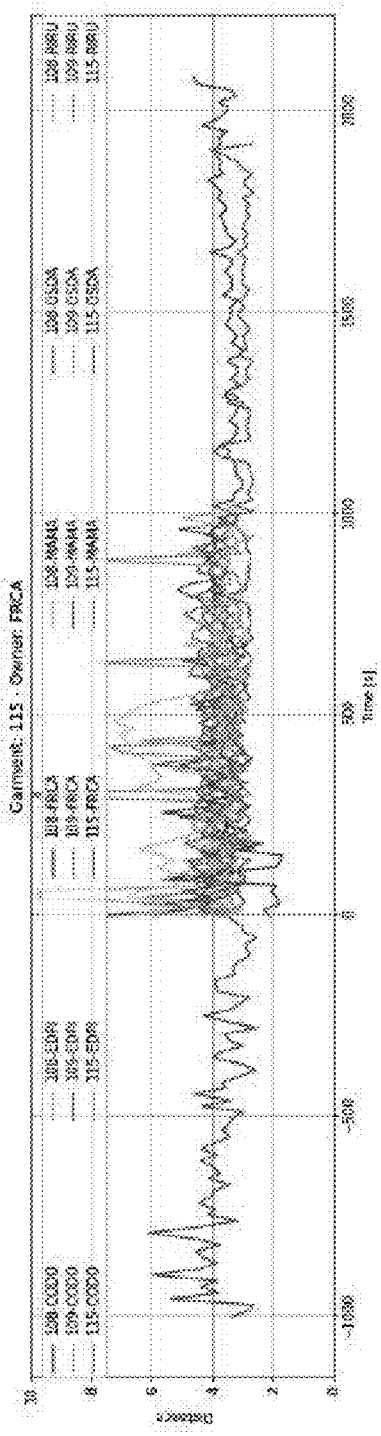

FIGS. 8A-8C illustrate the use of a 'best' feature. In FIGS. 8A-8C, the resulting distance using the best axis (i.e., most compact clusters) are shown. FIGS. 9A-9C show the distance using the worst axis (i.e., most spread clusters). The results shown in FIGS. 7A-7C (i.e., all the axis) indicate a better authentication of the user than the ones shown in FIGS. 8A-8C and 9A-9C. When using all the axis, the differences among users may be clearer making it easier to reject a user having higher distances in this particular example. Additional data may aid further distinguish this approach. FIGS. 9A-9C illustrate a method of approach using the 'worst' feature.

Also described herein are methods and apparatuses including the use of support vector data description. The Support Vector Data description (SVDD) deals with the problem of making a description of a training dataset with the aim of detecting which (new) data observations resemble this training set. This procedure is also known as one-class classification. Data description can be used for outlier detection, that is, to detect uncharacteristic data values from a data set. In many one-class classification problems there is a major complication, namely that it is beforehand not clear what the specific distribution of the data will be in practice. With SVDD, we obtain a spherically shaped boundary around the training dataset. We used SVDD to obtain those boundaries in the frequency domain of the accelerometer data, and then computed a confidence of being part of the training data. The plots below (FIGS. 10A-10F) show the confidence level (e.g., the bars) for different users using different garments. The highest bar corresponds to the training data, thus we expect that the second highest bar also corresponds to the same user, when wearing a different garment, which is the case for users MAMA, OSDA and RIRU.

FIGS. 10A-10F illustrate detection confidence for users MAMA, OSDA, and RIRU. The top ranking pair (user garment) corresponds always to the dataset that was used for training the model. We observed that the next high confidence results correspond to the same user.

FIGS. 11A-11F shows the detection confidence for users EDPI, FRCA, and CODO. The top ranking pair (user garment) corresponds always to the dataset that was used for training the model. We observe that both datasets corresponding to user EDPI are subject to overfitting as the model is not able to recognize the user wearing a different garment. On the other hand, the model corresponding to user CODO seems to be subject to under-fitting as most of the other users display a high detection confidence as well. In general, FIGS. 11A-11F show detection confidence for users EDPI, FRCA, and CODO.

Interestingly, we observed that the quality of the results in terms of prediction accuracy for both the positive class (the target user) and the negative class (all other users) does not depend on the amount of sensor considered. Indeed, the difference in accuracy with respect to the results presented above stays in the ballpark of +/−5% if we consider the signal of any individual sensor instead of all combined. Nevertheless, we suspect that this might not be the case if we were to repeat this experiment on a larger set of users. In this case, the probability of having similar signals among individuals would increase thus making the definition of unique user domains more difficult. With more sensors however, we are able to work in a higher dimensional space where overlaps are less likely and identification is therefore improved.

Although the examples descried herein use Dynamic Time Warping instead of Euclidean Distance, in some variations it may be more appropriate given that out-of-phase time series can match prototype time-series characterizing the authenticated user. For the second approach, the use of wavelet transforms instead of FFT may add time dependency to the models and may be useful.

In general, further tests including other sensors and a combination of model predictions (e.g., by using a Bayesian approach). The use of a larger collection of data for more accurate models may also be used. Testing the robustness and accuracy (e.g., test if a user can imitate the behavior of another one) of the model. Other kind of features may be used to characterize the signals being used to authenticate the user. For instance, based on theoretical-information measures indicating disorder (entropy), complexity, fractal dimension and chaos dimension may be used.

As illustrated, it is possible to build user-specific models of behavior from the available data, which indicates that authentication is feasible based on behavioral biometric data. Authentication is possible among this reduced group of people using all the IMU sensors in the garment.

This proof-of-concept is based on approaches using only one modality (accelerometer). This approach may be extended to a larger group or users, using multiple modalities and combining multiple machine learning-based authentication algorithms working in parallel.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of confirming a user's identity, the method comprising:
    wearing a garment comprising a plurality of integrated sensors at predetermined locations;
    synchronously recording sensor data from multiple predetermined locations on the garment;
    generating, in the garment, a biometric token from the recorded sensor data;
    transmitting the biometric token to a lodger in or on the garment; and
    transmitting the biometric token to a third party having a biometric template against which the biometric token may be tested.

2. The method of claim 1, wherein generating a biometric token from the recorded sensor data comprises generating the biometric token in a scheduler on the garment.

3. The method of claim 1, wherein wearing the garment comprises adjusting the position of the sensors based on haptic feedback from the garment.

4. The method of claim 1, wherein synchronously recording the sensor data comprises synchronously recording the sensor data from a plurality of motion sensors.

5. The method of claim 1, wherein synchronously recording the sensor data comprises synchronously recording the sensor data from a plurality of motion sensors, one or more respiration sensors and one or more electrodes configured to contact the user's skin when the garment is worn.

6. The method of claim 1, wherein wearing the garment comprises wearing the garment over the user's torso.

7. The method of claim 1, wherein synchronously recording the sensor data comprises synchronously recording the sensor data from multiple sensor types on the garment.

8. The method of claim 7, wherein synchronously recording the sensor data comprises recording the data at a plurality of frequencies.

9. The method of claim 1, further comprising encrypting the biometric token prior to transmitting the biometric token to the third party.

10. The method of claim 1, further comprising sending a coded message requesting approval of the user to proceed from the third party.

11. The method of claim 10, further comprising contacting an output on the garment to indicate agreement to the third party.

12. A method of confirming a user's identity, the method comprising:
- wearing a garment comprising a plurality of integrated sensors at predetermined locations in the garment that are configured to position the integrated sensors over the user's torso;
- synchronously recording sensor data from multiple predetermined locations on the garment, using a plurality of different sensor types;
- generating, in the garment, a biometric token from the recorded sensor data; and
- transmitting the biometric token to a third party having a biometric template against which the biometric token may be tested.

13. The method of claim 12, wherein generating the biometric token from the recorded sensor data comprises generating the biometric token in a scheduler on the garment.

14. The method of claim 12, wherein wearing the garment comprises adjusting the position of the sensors based on haptic feedback from the garment.

15. The method of claim 12, wherein synchronously recording the sensor data comprises synchronously recording the sensor data from a plurality of motion sensors.

16. The method of claim 12, wherein synchronously recording the sensor data comprises synchronously recording the sensor data from a plurality of motion sensors, one or more respiration sensors and one or more electrodes configured to contact the user's skin when the garment is worn.

17. The method of claim 12, wherein synchronously recording the sensor data comprises recording the sensor data at a plurality of frequencies.

18. The method of claim 12, further comprising encrypting the biometric token prior to transmitting the biometric token to the third party.

19. The method of claim 12, further comprising sending a coded message requesting approval of the user to proceed from the third party.

20. The method of claim 19, further comprising contacting an output on the garment to indicate agreement to the third party.

21. A method of confirming a user's identity, the method comprising:
- wearing a garment comprising a plurality of integrated sensors at predetermined locations in the garment that are configured to position the integrated sensors over the user's torso;
- adjusting the position of the sensors using haptic feedback from the garment;
- synchronously recording sensor data from multiple predetermined locations on the garment, using a plurality of different sensor types;
- generating, in the garment, a biometric token from the recorded sensor data;
- encrypting the biometric token; and
- transmitting the encrypted biometric token to a third party having a biometric template against which the biometric token may be tested.

* * * * *